United States Patent
Hayes et al.

(10) Patent No.: US 11,854,668 B2
(45) Date of Patent: Dec. 26, 2023

(54) ACCESSING DATA STORAGE PROVIDED USING DOUBLE-STRANDED NUCLEIC ACID MOLECULES

(71) Applicant: EVONETIX LTD, Cambridge (GB)

(72) Inventors: Matthew James Hayes, Cambridge (GB); Raquel Maria Sanches-Kuiper, Cambridge (GB)

(73) Assignee: EVONETIX LTD, Cambridge (GB)

( * ) Notice: Subject to any disclaimer, the term of this patent is extended or adjusted under 35 U.S.C. 154(b) by 580 days.

(21) Appl. No.: 17/261,271

(22) PCT Filed: May 29, 2019

(86) PCT No.: PCT/GB2019/051462
§ 371 (c)(1),
(2) Date: Jan. 19, 2021

(87) PCT Pub. No.: WO2020/021221
PCT Pub. Date: Jan. 30, 2020

(65) Prior Publication Data
US 2021/0280274 A1  Sep. 9, 2021

(30) Foreign Application Priority Data

Jul. 26, 2018  (GB) .................................... 1812169

(51) Int. Cl.
*G11C 25/00* (2006.01)
*G16B 50/00* (2019.01)
(Continued)

(52) U.S. Cl.
CPC ................ *G16B 50/00* (2019.02); *B01L 7/52* (2013.01); *C12Q 1/6844* (2013.01); *G06N 3/002* (2013.01);
(Continued)

(58) Field of Classification Search
CPC ......... G16B 50/00; B01L 7/52; C12Q 1/6844; G06N 3/002; G11C 11/54; G11C 13/0019; G11C 25/00
See application file for complete search history.

(56) References Cited

U.S. PATENT DOCUMENTS

2003/0228598 A1  12/2003  Mariella, Jr.
2010/0261228 A1*  10/2010  Gharib .................. C07H 21/04
536/25.3
(Continued)

FOREIGN PATENT DOCUMENTS

CN  102448977  5/2012
CN  106845158  6/2017
(Continued)

OTHER PUBLICATIONS

Office Action for TW Application No. 108119665 dated Mar. 23, 2023 and English translation, 35 pages.
(Continued)

*Primary Examiner* — Jay W. Radke
(74) *Attorney, Agent, or Firm* — NIXON & VANDERHYE P.C.

(57) ABSTRACT

Data storage is provided using double-stranded nucleic acid molecules provided on a thermal control device comprising a plurality of sites and temperature control circuitry to independently control a temperature of each of the plurality of sites. The temperature control circuitry, controls the site temperatures to provide a different temperature at a target site compared to other sites of the plurality of sites. The different temperatures at the target site and the other sites provide a greater probability of a read or write operation acting on the target site compared to the other sites. The temperature-based addressing helps to increase physical storage density.

25 Claims, 13 Drawing Sheets

(51) Int. Cl.
  *B01L 7/00* (2006.01)
  *C12Q 1/6844* (2018.01)
  *G06N 3/00* (2023.01)
  *G11C 11/54* (2006.01)
  *G11C 13/00* (2006.01)

(52) U.S. Cl.
  CPC .......... *G11C 11/54* (2013.01); *G11C 13/0019* (2013.01); *G11C 25/00* (2013.01)

(56) References Cited

U.S. PATENT DOCUMENTS

| | | | |
|---|---|---|---|
| 2014/0030170 | A1 | 1/2014 | Heimberg et al. |
| 2015/0103591 | A1 | 4/2015 | Sethi |
| 2018/0046921 | A1 | 2/2018 | Chen et al. |
| 2018/0189448 | A1 | 7/2018 | Bramlett et al. |
| 2020/0357483 | A1* | 11/2020 | Roquet .................. G16H 50/30 |
| 2021/0017595 | A1* | 1/2021 | Stakenborg .......... C12Q 1/6869 |
| 2021/0148872 | A1* | 5/2021 | Khurana ............ G11C 13/0019 |

FOREIGN PATENT DOCUMENTS

| | | | |
|---|---|---|---|
| CN | 110024037 A | * 7/2019 | ........... C12Q 1/6806 |
| WO | 2009/079856 | 7/2009 | |
| WO | 2015/144858 | 10/2015 | |
| WO | 2017/190297 | 11/2017 | |
| WO | 2018/104698 | 6/2018 | |

OTHER PUBLICATIONS

Masanori Arita, et al., "Chapter 38: DNA Memory", Handbook of Natural Computing, Jan. 1, 2012, pp. 1281-1318 (38 pages).

Md. Fakruddin, et al., "Nucleic acid amplification: Alternative methods of polymerase chain reaction", J Pharm Bioallied Sci., vol. 5, No. 4, Oct.-Dec. 2013, 17 pages, https://www.ncbi.nlm.nih.gov/pmc/articles/PMC331736/?report=printable.

S. M. Hossein Tabatabaei Yazdi, et al., "A Rewritable, Random-Access DNA-Based Storage System", Scientific Reports, vol. 5, published Sep. 18, 2015, 10 pages.

Lee Organick, et al., "Random access in large-scale DNA data storage", Nature Biotechnology, vol. 36, No. 3, Mar. 1, 2018, 9 pages.

Search Report for GB Application No. 1812169.9 dated Jan. 18, 2019, 4 pages.

International Search Report and Written Opinion of the ISA for PCT/GB2019/051462 dated Oct. 1, 2019, 17 pages.

* cited by examiner

ACCESSING DATA STORAGE PROVIDED USING DOUBLE-STRANDED NUCLEIC ACID MOLECULES

This application is the U.S. national phase of International Application No. PCT/GB2019/051462 filed May 29, 2019 which designated the U.S. and claim priority to GB Patent Application No. 1812169.9 filed Jul. 26, 2018, the entire contents of each of which are hereby incorporated by reference.

The present technique relates to the field of data storage provided using double-stranded nucleic acid molecules.

Information can be encoded in the sequence of base pairs that form a nucleic acid molecule, such as DNA, RNA or XNA. A desired sequence can be synthesized de novo in a factory or lab, to generate molecules which represent the data to be encoded. For example, with DNA molecules, each base in the sequence is one of four possible choices (adenine, cytosine, guanine or thymine), and so each base may encode two bits of information. Nucleic acid based data storage is an attractive option because the physical density is very high. With three to four orders of magnitude higher density than tape-based storage, a 1 exobyte datacentre could in principle be shrunk to the size of a pinhead.

At least some examples provide a method for accessing data storage provided using double-stranded nucleic acid molecules provided on a thermal control device comprising a plurality of sites and temperature control circuitry to independently control a temperature of each of the plurality of sites; the method comprising: controlling temperatures of the plurality of sites using the temperature control circuitry, to provide a different temperature at a target site compared to other sites of the plurality of sites; and performing a read operation to read data from one or more selected double-stranded nucleic acid molecules at the target site or a write operation to form one or more new double-stranded nucleic acid molecules encoded with data at the target site, where the different temperatures at the target site and the other sites provide a greater probability of the read or write operation acting on the target site compared to the other sites.

At least some examples provide a computer-readable program or data structure comprising instructions or control data for controlling an apparatus to perform the method discussed above.

The program or data structure may be stored on a recording medium. The recording medium may be non-transitory recording medium.

Further aspects, features and advantages of the present technique will be apparent from the following description of examples, which is to be read in conjunction with the accompanying drawings, in which.

Figure 3:
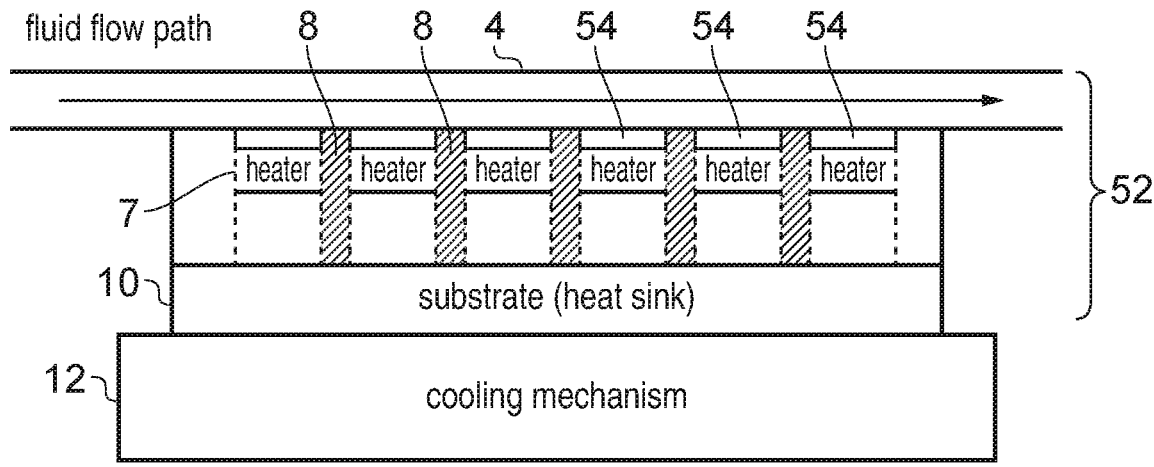
Figure 4:
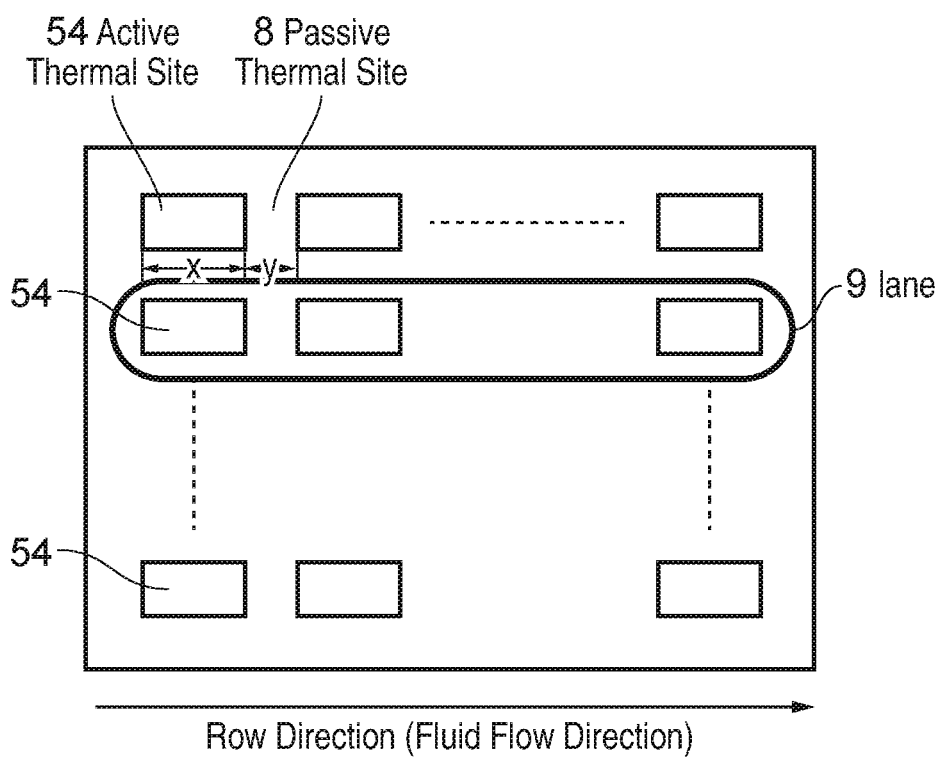
Figure 5:
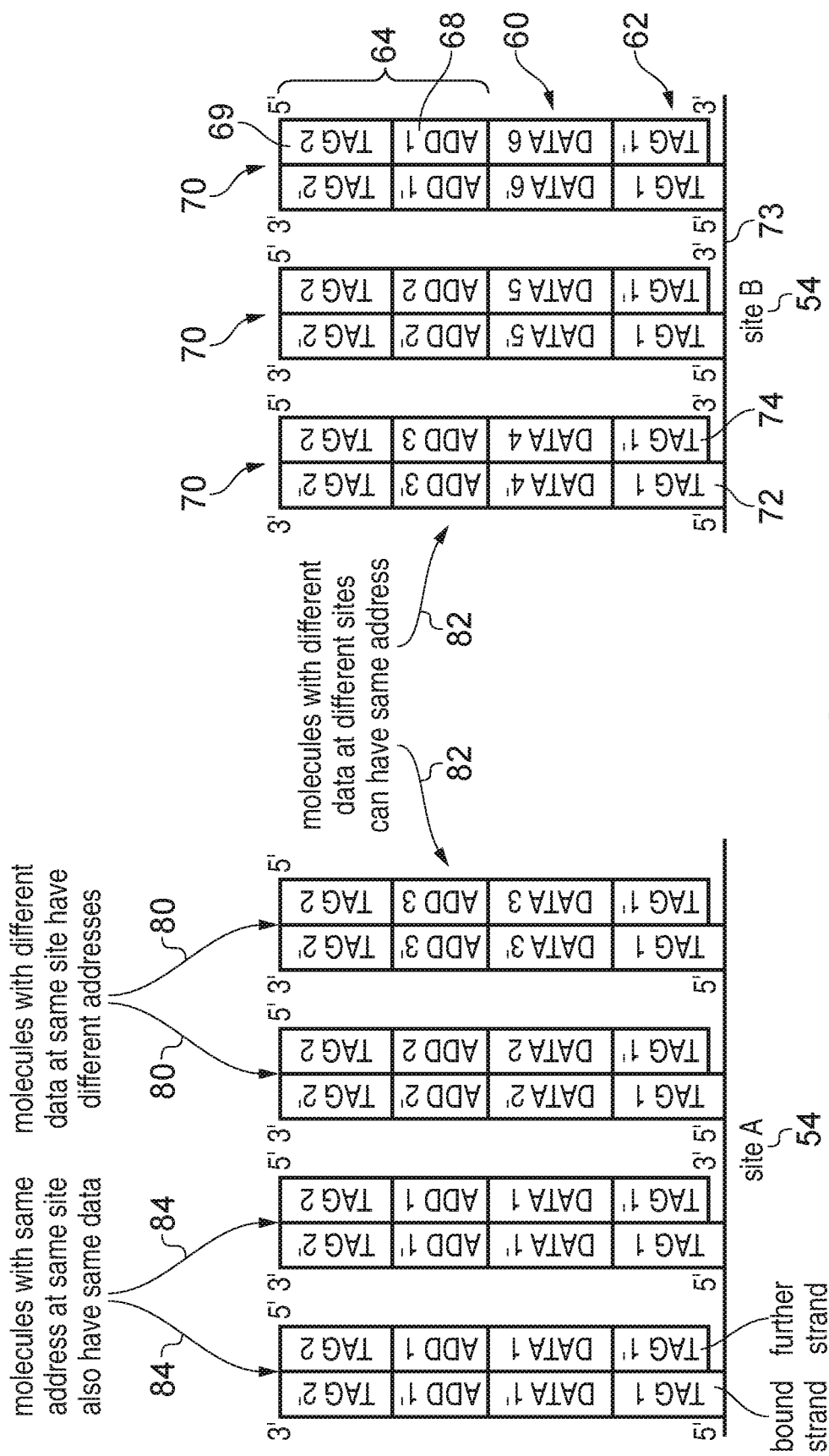
Figure 7:
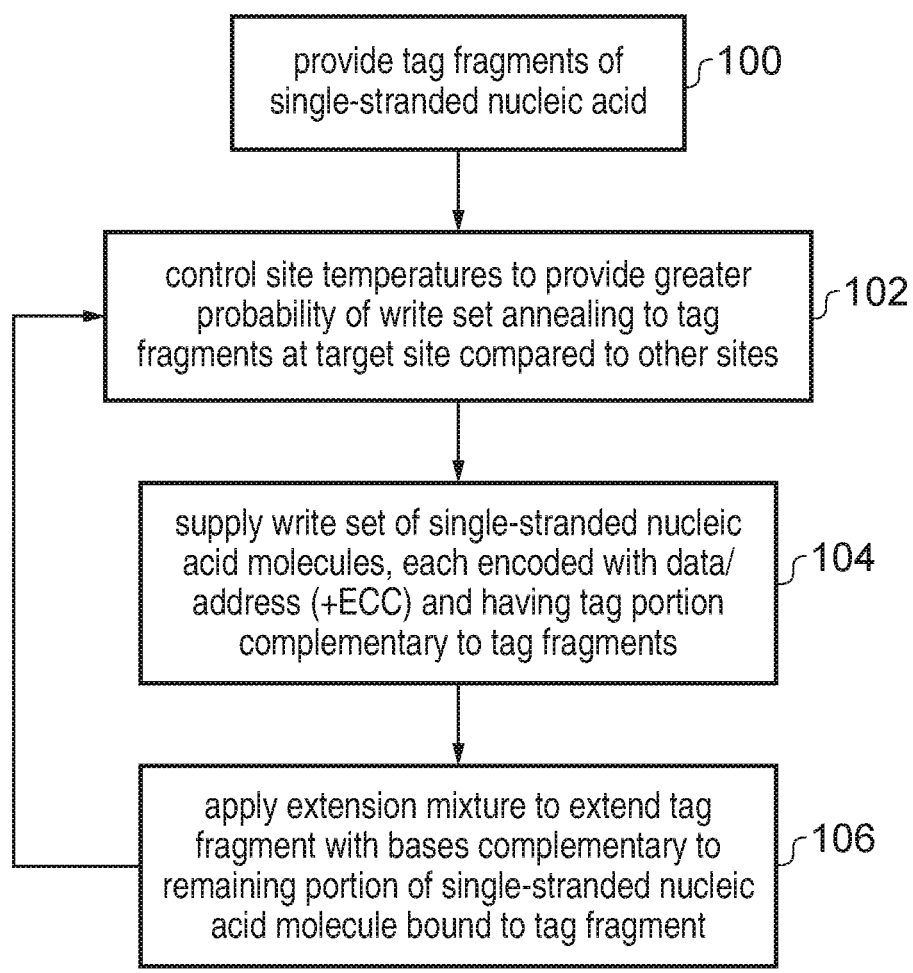
Figure 9:
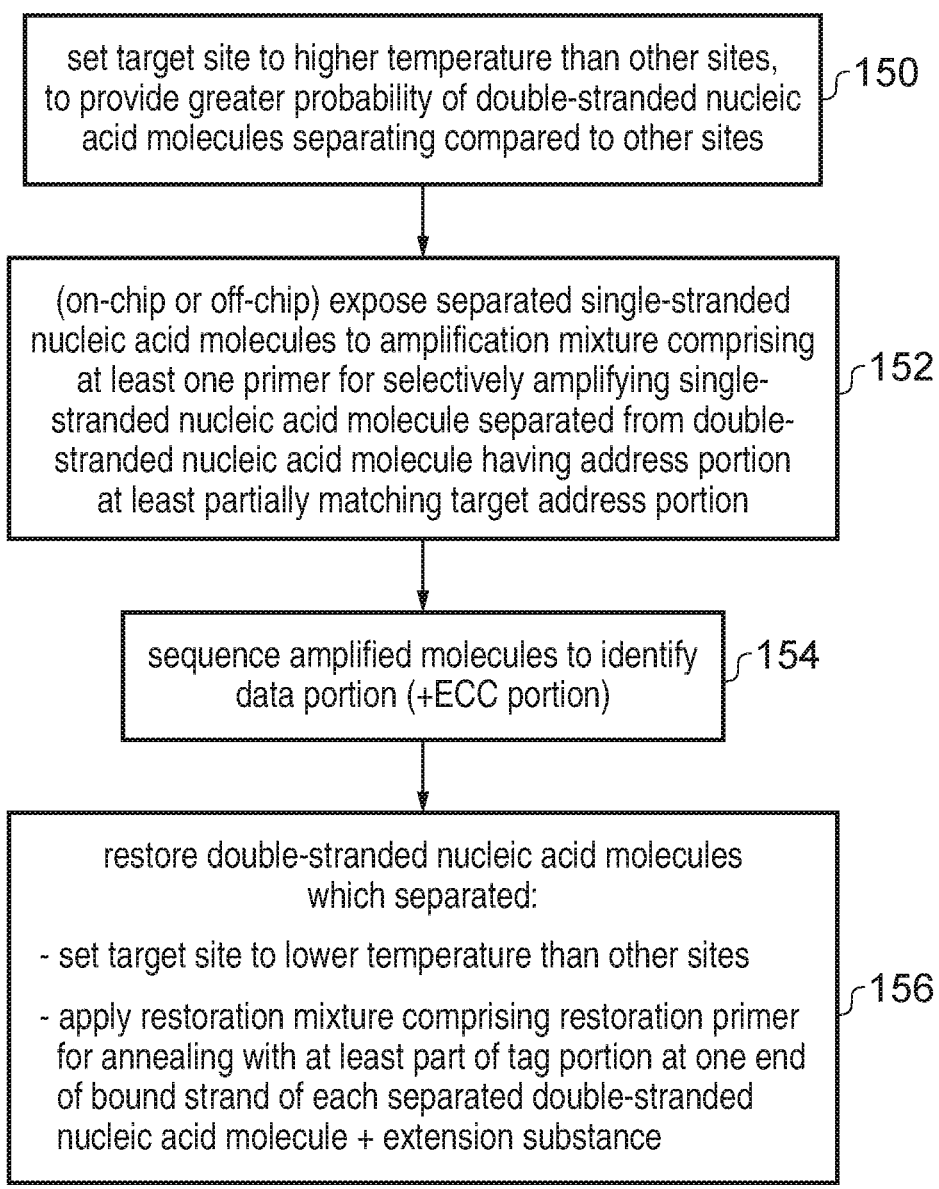
Figure 10:
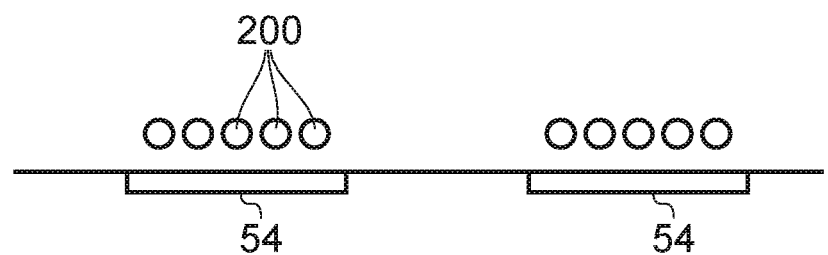
Figure 11:
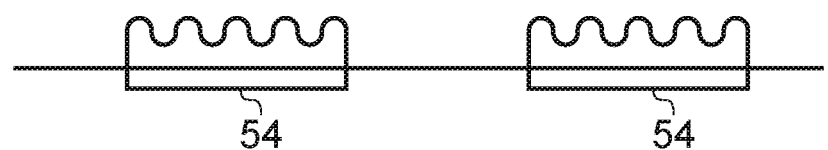
Figure 12:
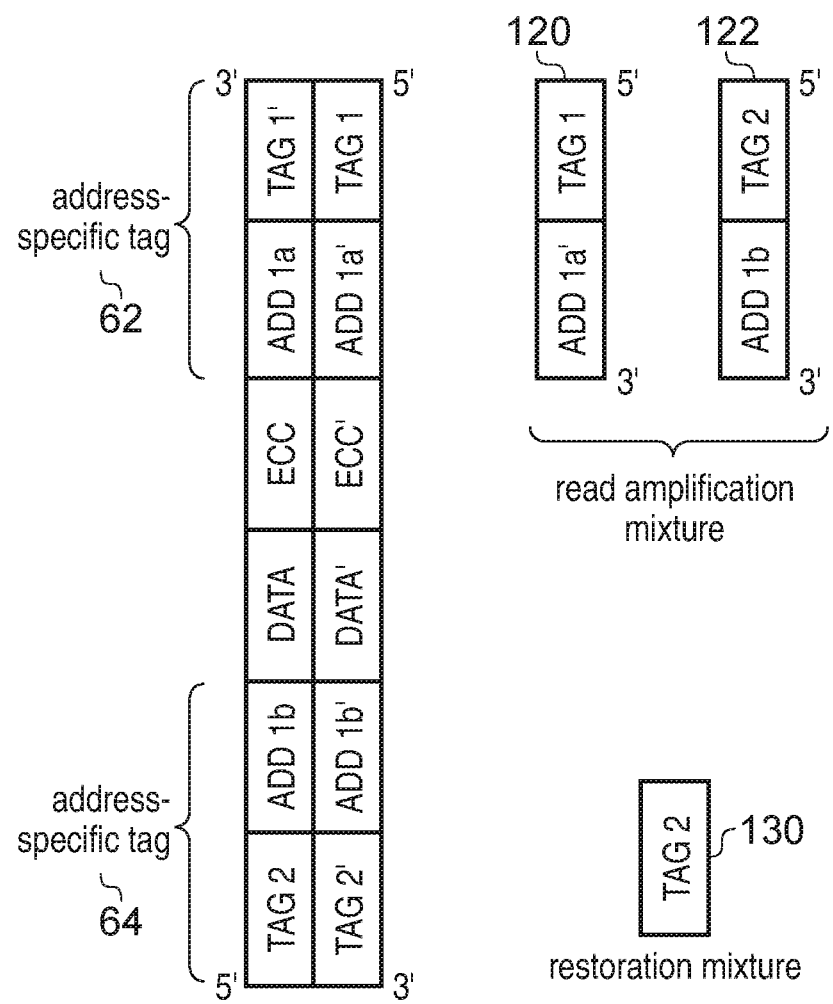

FIGS. 3 and 4 schematically illustrate the thermal control device;

FIG. 5 shows an example of double-stranded nucleic acid molecules allocated to different sites of the thermal control device;

FIGS. 6A to 6E illustrate a write operation for forming one or more new double-stranded nucleic acid molecules encoded with data;

FIG. 7 is a flow diagram illustrating a method of performing the write operation;

FIGS. 8A to 8D illustrate a read operation to read the data encoded in selected double-stranded nucleic acid molecules and a restore operation to restore double-stranded nucleic acid molecules that separate during the read operation;

FIG. 9 is a flow diagram illustrating a method of performing the read and restore operations;

FIGS. 10 and 11 show examples of structures for increasing the surface area available for attachment of nucleic acid molecules at a given site of the thermal control device; and FIG. 12 illustrates an example where address-specific tag portions are used at both ends of the encoded nucleic acid molecules.

The inventors recognised that, although in theory nucleic acid based data storage can offer the prospect of extremely high storage density, in practice such high density cannot yet be achieved with existing schemes for addressing selected nucleic acid molecules within a library of nucleic acid molecules representing the encoded data set. The probability of incorporation errors arising when synthesising nucleic acid molecules having a desired sequence increases with the length of the sequence, and so practically there may be a limit to the length of nucleic acid molecule that can be synthesised (even if error correction codes or other error detection techniques are used to include some redundancy within the sequence of information to allow for detection of such incorporation errors). This means that in order to use nucleic acid molecules to represent a data set of a reasonable size, in practice a library of different nucleic acid molecules with different encodings would be provided, which together represent the overall data set. Accessing such a library would require the ability to individually select particular nucleic acid molecules from the library in order to read the data in those nucleic acid molecules, without accidentally reading other nucleic acid molecules of the library which represent a different part of the data set from the part desired to be read.

It is possible to use amplification processes, such as PCR, to selectively extract and amplify double-stranded nucleic acid molecules which have part of their sequence matching a desired pattern as represented by a primer sequence. Different primers could be provided corresponding to different addresses to be accessed, to distinguish different parts of the data set. However, the number of unique primers that can be maintained may be limited to a certain number, and this limits the size of the data set that can be maintained. Hence, when a data set above a certain size needs to be encoded, a number of physically separate fluidic volumes would typically need to be maintained, so that molecules representing different portions of the data set may be provided with the same address portion in different physical wells so that the same primer can be reused across different wells. In practice, the physical separation of different parts of the data set into these physically separate wells requires additional space which greatly increases the overall size of the storage library. Hence this would detract from the very advantage of using nucleic acid molecules for data storage. This may make it hard for nucleic acid based data storage to produce significant density improvements compared to current data storage methods using magnetic tape or solid state memory for example.

In the technique discussed below the double-stranded nucleic acid molecules are provided on a thermal control device which has a number of sites, at which the nucleic acid molecules can be provided. The thermal control device includes temperature control circuitry for independently controlling the temperature of each of the sites of the thermal control device. Hence, one site can be set to a different temperature to another site by the temperature control circuitry.

When the data storage is to be accessed for either a read operation for reading data from selected double-stranded nucleic acid molecules at a target site of the thermal control device, or a write operation to form one or more new double-stranded nucleic acid molecules encoded with data at the target site, the temperature control circuitry is used to control the temperatures of the sites of the thermal control device to provide a different temperature at the target site compared to other sites of the thermal control device. The different temperatures at the target site and the other site provide a greater probability of the read or write operation acting on the target site compared to other sites.

By using temperature to control which sites of the thermal control device are subject to the read operation or write operation, then even if different sites include double-stranded nucleic acid molecules which cannot be distinguished by the read operation or the write operation if both sites were set at the same temperature, the different temperatures at the target site compared to other sites means that the read or write operation has a greater probability of acting on the target site compared to other sites so as to provide selectivity of access to the nucleic acid based storage device. This means that it is not necessary to provide physically separate fluid volumes for each site. Hence, the random access provided by the temperature-based addressing scheme provides a much larger volume of information to be interrogated for a given amount of storage area and number of primers than would be possible with other methods. This enables the density of storage to be improved.

The plurality of sites of the thermal control device may be at respective portions of a shared fluid well without a physical barrier blocking fluid from passing between adjacent sites. Hence, when introducing fluid to perform the read or write operation, it is not necessary to prevent the fluid being provided to sites other than the target site to be read or written. The read or write operation may comprise flowing fluid across at least two of the plurality of sites including the target site. By eliminating the need to physically separate the fluid(s) used to perform the read or write operation from non-selected sites other than the target site, this enables the storage density of the device to be greatly improved. For example, it is no longer necessary to include physically separated wells with barriers in between each well, and it is also unnecessary to include mechanical structures for selectively directing fluid onto individual sites. Instead, for example, the entire thermal control device including each of the sites could be located within a single shared fluid well and fluid can simply be passed over all of the sites, with the temperature-based addressing providing a greater probability of the read or write operation affecting the target site compared to the other sites, to provide random access to the library of nucleic acid molecules.

Each double-stranded nucleic acid molecule may be encoded to include at least a data portion and an address portion. The data portion may represent the actual information to be encoded within the double-stranded nucleic acid molecule. The address portion may represent a sequence which is used in the read operation to identify which of a number of different molecules having different address portions corresponds to the target part of the data set of interest. In some cases, the double-stranded nucleic acid molecules could also include other portions. For example, to guard against the risk of incorporation errors being introduced during the synthesis of double-stranded nucleic acid molecules, the molecules could also include an error correction portion which provides an error correction code providing some redundancy to enable errors in either the data or the error correction code to be identified. The error correcting code could be an error detecting code which only enables the error to be detected but does not permit the correct data value to be restored from the sequence in the erroneous molecule alone, or could be an error correcting code which enables both error detection and correction so that the original value can be restored from the combination of the data portion and the error correcting portion. Any known type of error correcting code may be used, e.g. Reed-Solomon codes. In some implementations, both the data and its error correction value could be jointly encoded as a single sequence of bases (rather than including separate sequences mapping to the data and error correction code respectively).

The allocation of double-stranded nucleic acid molecules to the different sites of the thermal control device may be performed so that double-stranded nucleic acid molecules with different data portions but the same address portion are provided at different sites of the thermal control device. On the other hand, the double-stranded nucleic acid molecules located at a given site which have different data portions also have different address portions. By ensuring that molecules encoded with different data have different address portions if they share the same site of the thermal control device, then this enables those molecules to be distinguished using primers and/or sequencing during a read operation. However, by enabling differently encoded molecules sharing the same address portion to be provided at different sites of the thermal control device, the same primers can be reused across different sites in the read operation, enabling the size of the data set able to be represented in a single shared fluid well to be increased for a fixed number of primers available, since the temperature control can be used to distinguish which of the molecules at different sites sharing the same address portion are intended to be read.

The double-stranded nucleic acid molecules stored on the thermal control device may be obtained in different ways. In some cases, a single-stranded nucleic acid molecule corresponding to each double-stranded molecule intended to be stored could be synthesised separate from the thermal control device itself using any known nucleic acid synthesis technique, and can then be introduced onto the thermal control device later during the write operation, as will be discussed in more detail below. Alternatively, the nucleic acid molecules could be grown on the thermal control device itself. Hence, any known technique for synthesising nucleic acid molecules can be used to create the nucleic acid sequences required to encode the data. The technique discussed above provides a means for addressing individual molecules of a nucleic acid library representing the encoded data set, regardless of the way in which those molecules were created originally.

When a read operation is performed, the temperature control may comprise setting the target site to a higher temperature than other sites of the thermal control device during at least part of the read operation. This provides a greater probability of the double-stranded nucleic acid molecules at the target site separating into single-stranded nucleic acid molecules, compared to other sites of the thermal control device. This means that amplification techniques which act on single-stranded nucleic acid molecules are more likely to amplify the molecules at the target site than the molecules at other sites.

The separated single-stranded nucleic acid molecules can be exposed to an amplification mixture that comprises at least one primer for amplifying a single-stranded nucleic acid molecule which has been separated from a double-stranded nucleic acid molecule having an address portion which at least partially matches a target address portion. The target address portion may be the address portion in the double-stranded nucleic acid molecules which are desired to be read. The amplified nucleic acid molecules amplified by the amplification mixture can then be sequenced to identify at least a data portion of the amplified nucleic acid molecules (and optionally also other portions such as the error correcting portion and/or part of the address portion). Hence, as the temperature control makes the molecules at the target site more likely to separate into single strands, and the amplification mixture includes a primer which has a greater probability of amplifying the single-stranded nucleic acid molecule separated from a double-stranded molecule having an address portion at least partially matching a target address portion than amplifying other single-stranded nucleic acid molecules, this increases the probability that the sequenced nucleic acid molecules are molecules having the target address portion which are desired to be read, thus enabling the random access.

It will be appreciated that it is not essential for the primer used in the amplification mixture to completely match the target address portion of the double-stranded nucleic acid molecules desired to be read. To increase the number of addresses possible for a given number of primers, the address portion could be larger than the portion of the sequence matched by the primer so that a number of different addresses could all be matched against the same primer, in which case the amplification may actually amplify nucleic acid molecules corresponding to a number of different addresses. This is acceptable if the sequencer can still distinguish the different addresses which match the same primer.

To support the read operation, each double-stranded nucleic acid molecule may include first and second tag portions at opposite ends of the double-stranded nucleic acid molecule. The first and second tag portions may be particular sequences of bases which are independent of the particular data being encoded into the double-stranded nucleic acid molecule within the data portion. At least one of the first and second tag portions may be an address-specific tag portion which includes at least part of the address portion of the double-stranded nucleic acid molecule. By including an address-specific tag portion in each double-stranded nucleic acid molecule, this enables the amplification mixture to selectively amplify the molecules having a particular address-specific tag portion which varies from molecule to molecule, enabling selectivity in the random read access.

The amplification mixture may comprise a first primer which is complementary to the first tag portion of a first strand of a double-stranded nucleic acid molecule having a target address portion, and a second primer complementary to the second tag portion of a second stand of the double-stranded nucleic acid molecule having the target address portion. By including both the first primer and the second primer this ensures that the primers may alternately amplify the first and second strands of each molecule respectively so as to rapidly increase the number of copies of the amplified molecules that are provided.

Complementarity is the principle affecting the binding of two single-stranded nucleic acids to form a double-stranded nucleic acid. It is a property shared between two nucleic acid sequences, such that when they are aligned antiparallel to each other, the nucleotides opposing each other in the two sequences will all be complementary for optimal binding. At the molecular level, complementarity is determined by optimal hydrogen bonding between specific base pairs. For example, in DNA, adenine is complementary to thymine, and guanine is complementary to cytosine; and in RNA, adenine is complementary to uracil, and guanine is complementary to cytosine. Complementary pairing of bases allows information to be copied from one molecule to another, and, in nature, from one generation of cells to another. Hence, two sequences of single-stranded nucleic acid may be considered to be complementary if there sequences are such that when they are aligned anti-parallel to each other, the opposing nucleotides in the two sequences are complementary enough that there is a sufficiently high probability of the two single-stranded nucleic acid sequences binding to each other. It is not essential for every base in one of the single-stranded nucleic acid molecules to be exactly complementary with the corresponding base in the other of the single-stranded nucleic acid molecules. Where the overlapping portions of the sequences are sufficiently long then a single base error or an error in a relatively small number of bases may be tolerated whilst still permitting binding of the respective single-stranded nucleic acid molecules. Hence, in this application the term "complementary" is intended to mean complementary enough that the relevant sequences of bases will bind or hybridise at the relevant operating temperature for the step being performed.

In one example implementation, only one of the first and second tag portions may be an address-specific tag portion as discussed above, and the other may be an address-independent tag portion which is the same of double-stranded nucleic acid molecules having different address portions at the same site. This may make the practical implementation of the memory device simpler to implement, since a selection from a single set of primers available for selection as the primer matching the address-specific tag portion can be enough to enable the selectivity of read access. For the other primer which corresponds to the address-independent tag portion, the same primer can be used regardless of which address portion is to be read. Hence, this may reduce the engineering complexity by enabling a single primer selection step.

In other example implementations, both the first and second tag portions of each double-stranded nucleic acid molecule may be address-specific tag portions which include at least part of the address portion of the double-stranded nucleic acid molecule. By making both tag portions address-specific, this provides additional selectivity so that the number of different addresses which can be distinguished by a given set of primers can be increased. This is because the selection of a particular address may then be based on the combination of a particular first primer selected from a set of possible first primers and a particular second primer selected from a set of possible second primers. For example, whereas an approach using address-specific tags at only one end of the double-stranded nucleic acid molecules could, using a given number of primers (e.g. 100), enable a certain number of addresses to be distinguished by the primers, if there is an address specific tag at both ends, then the same number of addresses could be distinguished using only 20 primers, since a combination of a primer selected from a first set of 10 primers and a primer selected from a set of a further 10 primers could then provide in combination the same effect as the 100 primers mentioned above. Hence, while there may be some additional engineering complexity in providing the hardware elements to select and combine different primers into the amplification mixture to be supplied for a given read operation, this approach can expand the size of the data set available to be represented for a given number of primers.

Hence, either one of the first and second tag portions, or both, may be an address-specific tag portion. For any address-specific tag portion, it can be useful to encode the address-specific tag portion using an address-dependent part which includes at least part of the address portion and an address-independent part which is the same for the double-stranded nucleic acid molecules having different address portions at the same site. While during the read operation the address-dependent part may be used to provide the selectivity of read access used to provide random access to a desired part of the data set, it can be useful to also include an address-independent part to simplify other operations performed on the thermal control device. For example, when attaching a new set of molecules to the target site during a write operation, or when restoring the set of double-stranded nucleic acid molecules after they have been separated in the read operation, it can be useful to provide an operation which affects all of the molecules at the same site even if they have different addresses. By including an address-independent part in the address-specific tag portion this makes the implementation of such operations which affect differently addressed molecules in common much more straightforward.

During the read operation the amplification of the separated molecules can be performed either on-chip or off-chip. Hence, in some examples the amplification mixture may be applied to the thermal control device to amplify the released single-stranded nucleic acid molecules locally on the thermal control device. Alternatively, the separated single-stranded nucleic acid molecules could be removed from the thermal control device and then the amplification mixture could be applied off-chip.

The amplification could be performed by a variety of methods. In some cases the amplification may be performed by PCR. Alternatively, an isothermal enzyme-based amplification could be used. In both examples, there may be a step of setting the target site to a higher temperature than other sites to provide a greater probability of separation of the double-stranded nucleic acid molecules into single-stranded nucleic acid molecules at the target site compared to other sites.

In cases where the amplification is performed locally on the thermal control device, where PCR is used then the controlling of the temperatures during the read operation may comprise thermal cycling of the target site through repeated cycles of heating and cooling. While the temperature at the target site is thermally cycled, other sites may be maintained at a temperature lower than a maximum temperature used in the thermal cycling. The thermal cycling at the target site means that when the temperature increases towards the maximum temperature in the cycle the double-stranded molecules are more likely to separate at the target site, while by holding other sites at a lower temperature this means that molecules at those sites are less likely to separate. However, by reducing the temperature at the target site when the temperature approaches the minimum temperature of the thermal cycle, then this means that the primers introduced in the amplification mixture are more likely to anneal to single-stranded molecules so that an extension mixture containing an extension enzyme and nucleotides can extend the primer so as to generate complementary sequences of bases to the sequence to which the tag is bonded, to provide replication of the sequences targeted by the primer.

On the other hand, if an isothermal enzyme-based amplification method is used, then the temperatures may be controlled so that, during the amplification (having already separated the double-stranded nucleic acid molecules into single-stranded nucleic acid molecules at the target site), the target site is set to a temperature greater than or equal to an activation temperature of at least one amplification enzyme. Once the double-stranded nucleic acid molecules have separated at the target site, it is no longer necessary to hold other sites at a colder temperature than the target site, as the enzyme-based amplification method may amplify single-stranded nucleic acid molecules, but not double-stranded molecules which were not separated. Some isothermal amplification methods may require more than one amplification enzyme or can provide accessory proteins or complexes which control the activation of the amplification enzyme. Examples of such isothermal enzyme-based amplification methods are discussed in M. Fakruddin et al. "Nucleic acid amplification: Alternative methods of polymerase chain reaction." Journal of pharmacy & bioallied sciences 5.4 (2013): 245.

As discussed above, the read operation includes controlling the temperatures to increase the probability of double-stranded nucleic acid molecules being separated into single-stranded nucleic acid molecules at the target site compared to other sites. It can be useful to store double-stranded nucleic acid molecules on the thermal control device as these are more stable than single-stranded molecules, but the separation into single-stranded nucleic acid molecules may be needed to enable the amplification mixture to take effect. However, once the read operation is carried out then there may be separated single-stranded molecules remaining at the target site, including not only the molecules which correspond to the required addresses to be read but also other molecules corresponding to different addresses at the same target site.

The read operation may include restoring the double-stranded nucleic acid molecules which were separated into single-stranded nucleic acid molecules. Hence, the read operation may be a non-destructive operation. This is useful as it avoids any need to re-write previously separated molecules after the read is complete, which helps to reduce the volume of nucleic acid sequences synthesised off-chip which are needed, reducing wastage of the previously synthesised molecules which are present on the thermal control device.

Each double-stranded nucleic acid molecule may comprise a bound strand which is bound to a surface at one of the sites and a further strand which is hybridised to the bound strand. The further strand can also be referred to as the "loose" strand below. When the single strands of the double-stranded nucleic acid molecule separate then the bound strand will remain bound to the surface but the further loose strand will separate and may flow away within fluid being passed over the sites. The restoring may comprise applying a restoration mixture which comprises a restoration primer for annealing with at least part of a tag portion at one end of the bound strand for each separated double-stranded nucleic acid molecule. Once the restoration primer has bound to the tag portion of the bound strand, an extension mixture (e.g. containing an extension enzyme and nucleotides) may be provided to extend the primer sequence with bases complementary to the remaining part of the bound strand, so as to restore the further strand which previously decoupled from the bound strand during the read operation. It can be useful to provide a tag portion which includes an address-independent part which is the same for molecules having different address portions at a given site, with the restoration primer being complementary to the address-independent part, so that only one primer type is needed for performing the restoration operation. During the restoring (in particular during primer annealing), the target site may be maintained at a lower temperature than other sites. This makes it more likely that the restoration primer anneals to the tag portion in the bound strands remaining at the target site following the read, compared to other sites. Hence, following a read the molecules can be restored to the state they were in before the read operation was performed, to provide a non-destructive read process.

On the other hand, for a write operation being performed to form one or more new double-stranded nucleic acid molecules encoded with data at the target site, the target site may be maintained at a lower temperature than other sites, to provide a greater probability of the new double-stranded nucleic acid molecules being formed at the target site compared to other sites. By reducing the temperature at the target site this makes it more likely that there will be binding between the introduced set of molecules and the target site.

The write operation may comprise providing tag fragments of single-stranded nucleic acid which are bound to the surface at the target site. The binding of tag fragments to a surface may be performed by growing or synthesising the tag fragments at the target site themselves, or by introducing the tag fragments in a flowing fluid passed across the target site and using surface chemistry to attach the tag fragments to the surface of the target site. In some cases, the step of providing the tag fragments need not be performed at the time of supplying the write set of single-stranded nucleic acid molecules themselves. For example the tag fragments may already have been supplied earlier. For example, when the thermal control device is first prepared for the very first write operation, tag fragments could be provided and attached at every site of the thermal control device, ready for a subsequent write operation to be performed later. Hence, at the time of the write operation the tag fragments are provided, but the actual time of attaching the tag fragments to the surface could have been done earlier or could be done immediately before the write operation itself.

During the write operation, a write set of single-stranded nucleic acid molecules is supplied. The write set of single-stranded nucleic acid molecules is encoded with sequences corresponding to the new double-stranded nucleic acid molecules to be formed. As discussed above, the write set of single-stranded nucleic acid molecules could be synthesised off-chip by any known nucleic acid synthesis process. Each of the write set of single-stranded nucleic acid molecules includes a tag portion which is complementary to the tag fragments bound to the surface at the target site. By providing a different (lower) temperature at the target site compared to other sites there is a greater probability of the write set of single-stranded nucleic acid molecules annealing to the tag fragments at the target site compared to other sites. Hence, even if there is no ability to individually direct the single-stranded nucleic acid molecules to a particular site, the temperature control makes the write set of molecules more likely to bind to the target site than other sites, to provide the addressing required for random write access to the nucleic acid based memory device.

The write operation may comprise applying an extension mixture to extend each tag fragment with bases complementary to a remaining portion of the single-stranded nucleic acid molecule that annealed to the tag fragment, to form a corresponding double-stranded nucleic acid molecule. The extension mixture could include an extension substance, for example polymerase or another enzyme, and dNTPs (deoxyribonucleotide triphosphates). Hence, once the write set of single-stranded nucleic acid molecules have bound to the tag fragments the extension mixture can then fill in the remaining bases so as to form double-stranded nucleic acid molecules encoded with sequences corresponding to the supplied write set of single-stranded nucleic acid molecules. These new double-stranded nucleic acid molecules may have different data portions and different addresses as discussed above. Hence, during the write operation the write set of single-stranded nucleic acid molecules and the extension mixture may be exposed to at least two sites of the thermal control device including the target site. There is no need for a physical barrier between sites. This improves the density available for data storage.

In some examples, the thermal control device may include a substrate and the different sites of the device may be disposed at respective locations on the substrate. Each site may include at least one attachment surface for attaching single or double stranded nucleic acid molecules.

In some implementations a total surface area of the at least one attachment surface at a given site may be greater than an area of a projection of the given site onto the plane of the substrate. This could be achieved in different ways. In some examples one or more beads could be attached to the substrate or immobilised just above the substrate (e.g. using electrostatic or magnetic fields). In another example the site surface could be patterned with a three-dimensional pattern to increase the effective surface area of the surface compared to the area of the projection of the given site onto the plane of the substrate. Regardless of how the increased effective surface area is implemented, this provides more space for attachment of nucleic acid molecules, which can increase the density of data storage provided.

In one example, the thermal control device may include a number of active thermal regions disposed at respective locations on the substrates. Each active thermal region may include a heating element for applying a variable amount of heat to a corresponding one of the sites and a thermal insulation layer disposed between the heating element and the substrate. One or more passive thermal regions may be disposed between the active thermal regions and the substrate. Each passive thermal region may include a thermal conduction layer for conducting heat to the substrate. The thermal conduction layer of the one or more passive thermal regions may have a lower thermal resistance in a direction perpendicular to a plane of the substrate than the thermal insulation layer of the active thermal regions. Each site of the thermal control device as discussed above may correspond to one of the active thermal regions.

When in use, the substrate can act as a heat sink (either by having the substrate exposed to room temperature, or by providing cooling of the substrate if lower temperatures are required). Hence, the thermal conduction layer in the passive regions enables the passive regions to provide cooling of the medium in the regions between the active thermal sites, so that fluid passing over the sites can be cooled to a given temperature with less cooling provided at the active thermal sites themselves. This enables the active thermal sites to be designed to be more efficient for heating, since a thermal insulation layer which has a higher thermal resistance can be used between the heating element and the substrate as it is no longer required to allow so much heat to pass to the substrate to support cooling. This means that during heating less heat is lost to the substrate and therefore the overall temperature range supported by the device can be higher than an alternative approach which provides a number of active sites which are the sole source of heating and cooling.

A computer program or computer-readable data structure may be provided which comprises instructions or control data for controlling an apparatus to perform the method discussed above. For example the program or data structure may specify the timings and levels at which temperatures at the respective sites are to be adjusted, to control the read or write operations for reading or writing data at a given target site. The computer program could also control the selection of particular primer mixtures to be used in the read process. The program may be stored on a computer-readable storage medium, which may be a non-transitory storage medium.

This application describes a device capable of storing and retrieving digital information encoded within a multitude of nucleic acid (e.g. DNA, RNA or XNA) fragments. Information is written by introducing multiple nucleic acid fragments to the device, which are then stored in one of many addressable sites. The information can be retrieved non-destructively from any site by providing copies of the stored nucleic acid, which can then be sequenced. Information can be erased by releasing the stored nucleic acid from any site. The random-access afforded by the site-based addressing scheme permits a much larger volume of information to be interrogated than would be possible with other storage methods.

The examples discussed below use DNA as a particular example of nucleic acid molecules used to represent the data storage. It will be appreciated that other forms of nucleic acid could also be used, such as RNA or XNA.

Figure 1:
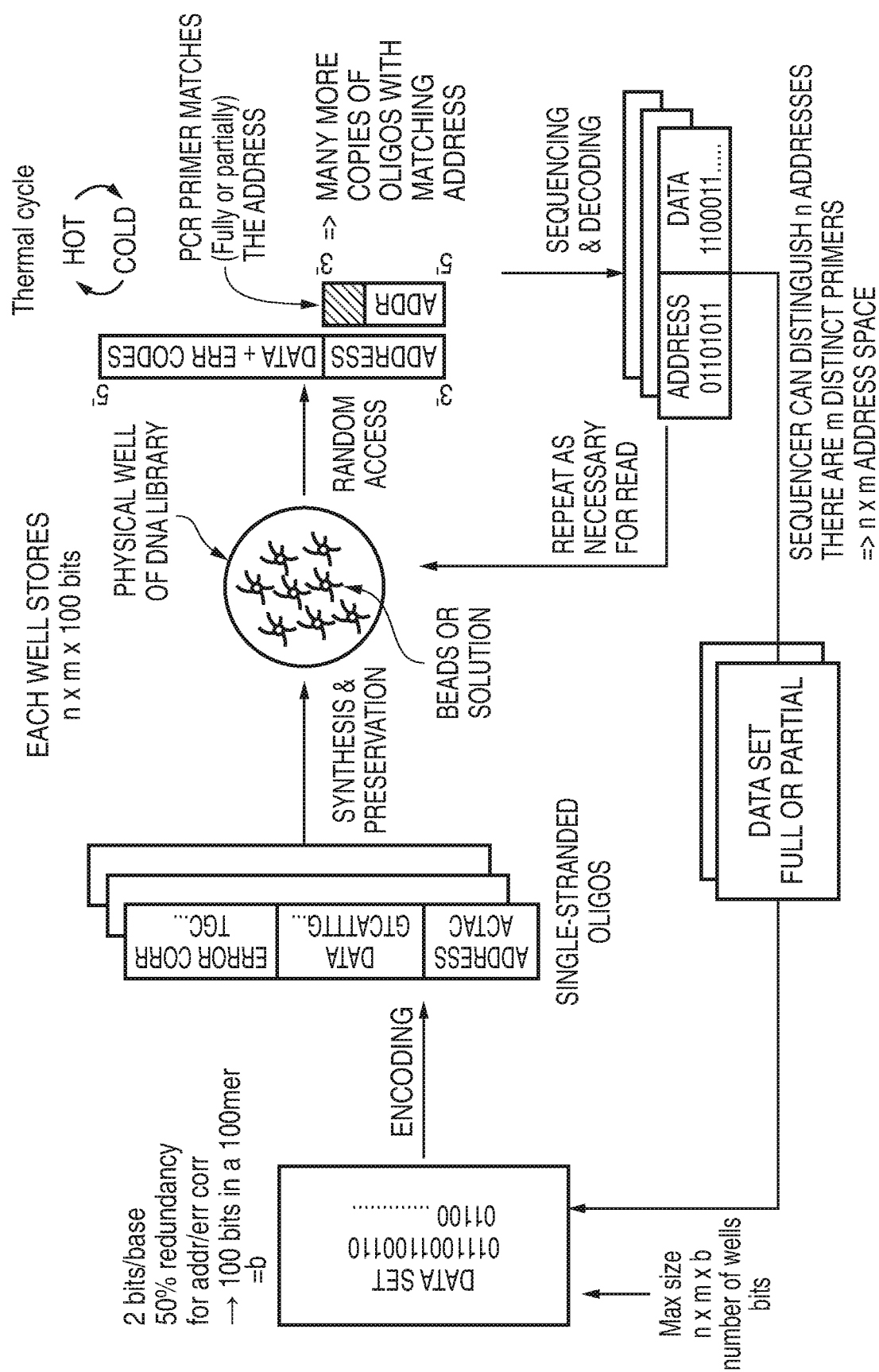
FIG. 1 shows a comparative approach for accessing data storage provided using nucleic acid molecules.

Information can be encoded in the sequence of base-pairs that comprise DNA molecules; each base is one of four possible choices and so encodes 2 bits of information. Molecular storage of information is attractive because the physical density is so high; with 3 to 4 orders of magnitude higher density than tape, a 1 EByte data-centre could in principle be shrunk to the size of a pin head. FIG. 1 shows for comparison an approach where the information is written and retrieved in several steps:
  1) Encoding. The data to be written is split up into small chunks, which can fit on short sections of DNA. The encoding must also include error-correcting coding schemes to compensate for the inevitable errors in both reading and writing, and an addressing scheme to identify the chunks position in the original data set.
  2) Synthesis. The individual DNA fragments are physically realised using DNA synthesis technologies.
  3) Preservation. The synthesised DNA is stored, using a combination of temperature, atmosphere or other methods to avoid degradation.
  4) Random access. To read back any desired portion of the data, the DNA fragments encoding the desired chunks must be identified. This can be achieved with PCR amplification using primers that are the complement of the address of the desired chunks; therefore, only the desired DNA is amplified.
  5) Sequencing. The amplified DNA is sequenced using next-generation sequencing technologies.
  6) Decoding. The measured sequence is re-arranged into the desired portion of the original data set, using the redundant error-correcting codes to ensure data integrity and the address codes to determine the order.

A significant limit to the scalability of this process is the need to have unique primers for each address range within the random-access scheme, which limits the size of the overall data set. Above a certain size, individual fluidic volumes must be maintained and sampled, with hardware that drastically reduces the information density achievable.

If the number of bits that can be represented in one DNA molecule is b, the number of different addresses that can be distinguished by the sequencer is n and the number of distinct primers available for performing PCR is m then the maximum size of the data set that can be represented within a single physical well of a DNA library using the conventional approach shown in FIG. 1 is n×m×b number of bits. If, for example, b=100, n=1000 and m=10000 then this means a million bits per physical well i.e. around 122 MB per well. Hence, in order to represent a data size of a significant size such as an exobyte volume of data corresponding to a typical data centre, the DNA library would need many physical wells, e.g. around $8 \times 10^9$ wells for an exobyte of storage. As the wells may be 10 to 12 orders of magnitude larger than the size of the DNA molecules themselves, then clearly it is no longer possible to shrink the data centre into the size of a pinhead as is often claimed for DNA based data storage. The need for physical separation of distinct physical wells so that the primers can be introduced only to a selected well and not into other wells, means that the storage density advantage of DNA based storage is eliminated. This makes it hard to provide a practical storage facility in DNA based data storage.

Figure 2:
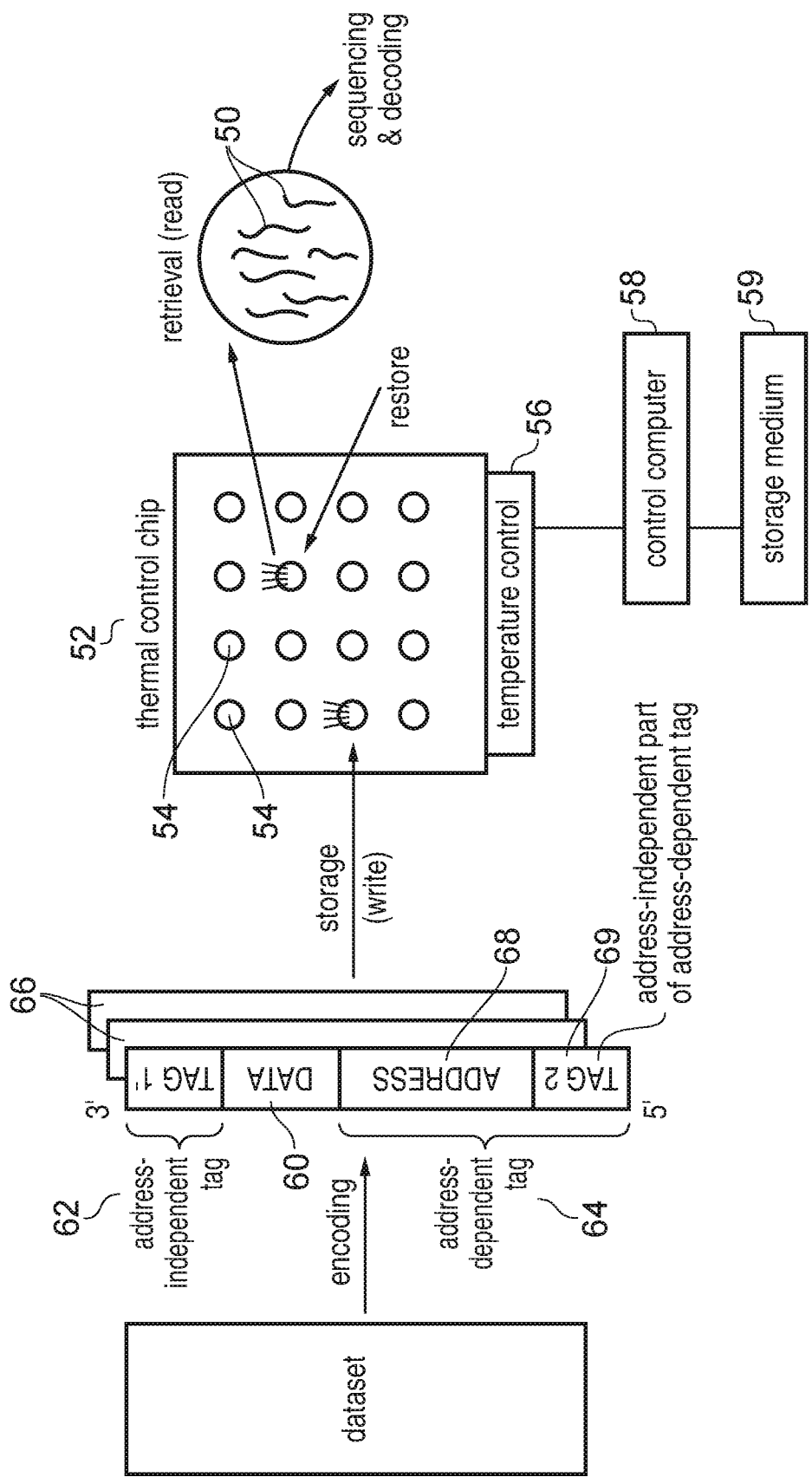
FIG. 2 shows a principle of accessing nucleic acid based data storage using a thermal control device which enables temperature-based addressing of the double-stranded nucleic acid molecules.

As shown in FIG. 2, the issues discussed above can be addressed by providing DNA molecules 50 on a thermal control chip 52 which has a number of independently addressable sites 54, each site capable of having attached to it a number of DNA molecules. Temperature control circuitry 56 is provided to independently control the temperature of each of the sites 54. Heating a given site 54 to a given temperature also heats the volume of liquid disposed above that site within a fluid flow cell that flows fluid over the surface of the thermal control chip 52. As discussed below, the effective surface area of these sites can be increased, e.g. by immobilising small beads above each site or by patterning the surface of each site to provide a three-dimensional pattern. Adjacent sites on the thermal control chip 52 are not separated by any physical barrier and so fluid supplied to one site 54 may also pass over other sites. Hence it is not necessary to use physical separation to ensure that a given site is selected. Instead the temperature control provided by the temperature control circuitry 56 can be used to select individual sites to/from which data is to be written/read. A control computer 58 may send control signals to the temperature control circuitry 56 defining the temperatures at which the various sites are to be set and the timings at which certain temperatures are to be applied. A computer program or data structure stored in a storage medium 59 may control the control computer 58 to apply the appropriate control signals to the temperature control circuitry 56 for performing a given read or write operation.

With the approach shown in FIG. 2, the encoding of the data set into DNA oligos may be similar to that shown in FIG. 1. While the error correction portion of the sequence is not explicitly shown in FIG. 2, it may still be provided. However, with the approach shown in FIG. 2, in addition to the data portion 60 (which may also include the error correction portion), the oligos are also encoded with first and second tag portions 62, 64 at either end of the single-stranded DNA molecules 66. In this example the first tag 62 is an address-independent tag portion which does not include any portion of the address of the DNA molecule. Hence the first tag 62 (at the 3' end of each encoded oligo) may be the same for each of the encoded single-stranded DNA molecules 66. On the other hand, the second tag 64 (at the 5' end) is an address-dependent tag portion 64 which differs from oligo to oligo. In this example the address-dependent tag includes an address-dependent portion 68, which in this example includes the full address portion identifying the address of the corresponding oligo, and an address-independent portion 69 which is the same for each of the oligos. The first and second tag portions are used to support read and write operations as will be discussed in more detail below.

It will be appreciated that each of the data portions 60, address portions 68 and first and second tags 62, 64 comprise a certain sequence of nucleobases, e.g. A, G, T or C in the case of DNA (or other types of bases in the case of other forms of nucleic acid).

FIGS. 3 and 4 illustrate a device 52 on which the data storage process discussed above can be performed. As shown in FIG. 3, a fluid flow element (e.g. a pump) is provided to control the flow of fluid through a fluid flow path 4 across the top of the device 52. A number of sites 54 for storing nucleic acid molecules are provided at various locations across the plane of the temperature control device 52. The top of each site 54 may include a surface material (e.g. a gold cap) which supports growth or attachment of nucleic acid molecules. Each site 54 corresponds to part of a continuous surface, with no physical barrier blocking fluid from passing between adjacent reaction sites 54. Each site 54 has a heating element 7 provided below the site surface to apply heat to the corresponding part of the fluid flowing over that site, to control the temperature of the fluid for adjusting the probability of read/write operations taking effect at that site. As shown in FIG. 4, the sites 54 are arranged in a two-dimensional matrix (grid), arranged in two or more rows (lanes) 9 where the lane/row direction is parallel to the direction that fluid flows through the fluid flow path 4. The regions lying between the sites 54 form one or more passive thermal regions 8 which do not comprise any heating element, but provide passive cooling by conducting heat away from the fluid towards the substrate 10 of the device 52. The length x of each active thermal site 6 in the row direction is longer than the length y of each passive thermal region 8 lying between a pair of adjacent active thermal sites 6 in the same row. As shown in FIG. 3, a cooling mechanism 12 may be provided to cool the substrate 10 to act as a heat sink.

The sites 54 are active thermal sites at which both heating and cooling can be provided. The flow of heat away from the site 54 by conduction to the cooler substrate 10 provides cooling. The heater (e.g. a resistive heating element) can be controlled to vary the amount of heat supplied. Hence, when the heat flow from the heater 7 is greater than the cooling flow of heat to the substrate, the net effect is that the site 54 is heated, while when the heat flow from the heater 7 is less than the cooling flow to the substrate, the net effect is that the site 54 is cooled.

The thermal resistance of the material provided below each active thermal site 54 in a direction perpendicular to the substrate may be greater than the thermal resistance in the direction perpendicular to the substrate of the material provided below each passive thermal region 8. The provision of passive regions having greater thermal conductivity than the active thermal sites 54 means that more of the cooling effect can be provided by the passive thermal regions 8, so that the active thermal sites 54 can be designed to be more efficient for heating. This allows a thermal insulation layer with greater thermal resistance to be provided between the heating element and the substrate, so that less heat has to be applied by the heater 7 to counteract the cooling flow to the substrate, and hence a greater overall temperature range can be supported by the device for a given maximum power of the heater 7.

Further details of the design of the temperature control device 52 may be found in the published PCT application WO 2018/104698 A1 by Evonetix Ltd. of Little Chesterford, UK, which describes in more detail examples of how to control the current to each heater 7 in each active thermal site so as to provide a desired temperature in the fluid above, and also describes examples of how to design the material below each active thermal site 6 so that it has a greater thermal resistance in the direction perpendicular to the substrate than the material provided below each passive thermal region 8 (e.g. a material comprising pillars and voids can be used).

Hence, in general the thermal control device is able to set different temperatures to each site 54 of the chip. The spacing x+y between adjacent sites may be much smaller than the spacing between physical wells that would be possible in a DNA library reorganised according to the approach shown in FIG. 1. For example, with an approach using separate physical wells, each well may need to be of a size of several millimetres across and there may need to be a physical barrier between each well which may also be a few millimetres in size, whereas with the thermal control device the pitch of the sites 54 may be sub-millimetre scale, e.g. micrometre scale or even smaller. This enables a great improvement in the storage density. For example, with b=100, n=1000 and m=10000 as in the example above, the approach shown in FIG. 2 is able to support 1.2 TB of data storage in a thermal control chip with 10000 sites 54, in a much smaller space than if physically separated wells capable of individually being supplied with fluid were used.

FIG. 5 shows how the DNA molecules provided at each site may be encoded. For conciseness FIG. 5 only shows two sites, site A and site B. At each site a number of double-stranded DNA molecules 70 are provided. Each double-stranded DNA molecule includes a bound strand 72 of single-stranded DNA which is bound to a surface 73 at the corresponding site 54. The bound strand is bound to the surface 73 at its 5' end (with the 3' end of the bound strand furthest from the surface 73). For ease of reference in FIG. 5 the surface 73 is shown as a flat surface but it will be appreciated from the examples shown in FIGS. 10 and 11 below that the surface does not need to be flat. Each double-stranded DNA molecule 70 also includes a further (loose) strand 74 of single-stranded DNA which is not bound to the surface 73 at the site, but is bound (hybridised) to the bound strand 72 (the loose strand having the 3' end closest to the surface 73 and the 5' end furthest from the surface 73). In the illustration in FIG. 5 and in subsequent drawings, to distinguish between the bound and loose strands 72, 74, a small gap is shown between the bottom of loose strand and the surface 73 at the site 54. This is not intended to imply that the loose strand 74 is necessarily a shorter sequence of bases than the bound strand 72. Rather, the gap shown in the drawings is merely for illustrative purposes to help distinguish which strand is bound and which strand is loose.

As shown in FIG. 5, each double-stranded DNA molecule may be encoded to include the first tag portion 62, the data portion 60 and the second tag portion 64 (including the address-independent part 69 and the address-dependent part 68 as discussed above). The bound and loose strands 72, 74 have complementary sequences of bases. The complementary parts of the sequence in the respective strands are shown with the same label (e.g. TAG 1, DATA 1, ADD 1, etc.) but with one of the strands including the main version of the sequence and the other of the strands including a complementary version marked with an apostrophe.

As shown in FIG. 5, DNA molecules which are provided at the same site 54 but have different data portions 60 also have different address portions 68. For example, the molecules marked with arrows 80 in FIG. 5 have different data portions (DATA 2 and DATA 3) and also have different address portions (ADD 2 and ADD 3). However, molecules which have different data portions at different sites 54 can have the same address portion. For example the DNA molecules 70 marked with arrows 82, one at site A and the other at site B, each have the same address portion (ADD 3) but have different data portions (DATA 3 and DATA 4). The molecules at different sites can share the same address portion because the temperature control applied to the different sites can be used to provide the random access selectivity for distinguishing these molecules.

As shown with the molecules labelled with arrows 84 in FIG. 5, it is possible for multiple versions of exactly the same DNA molecule to be provided at the same site, which share both the same data portion (DATA 1 in this example) and the same address portion (ADD 1). In practice, when writing new data to a given site of the thermal control chip 52, multiple instances of each encoded single-stranded sequence may be provided so that a given site may end up storing multiple copies of the same molecule which can help to provide robustness against errors. Hence, while in the examples discussed below, for conciseness each distinct sequence of DNA is shown only once or twice at a given site, it will be appreciated that each of those sequences could be duplicated multiple times at the same site.

While DNA molecules are stored at a given site of the thermal control chip 52, a preservation technique may be applied on-chip to increase the longevity of the DNA molecules. For example, examples of techniques that could be used to preserve the DNA molecules on the thermal control chip 52 may include any one or more of the following:
  drying and storing at ambient temperature (e.g. using air drying or freeze drying);
  preservation using a solution-based formula high in salts (e.g. DMSO/EDTA/saturated sodium chloride);
  storage at low temperatures (e.g. 4° C., −20° C., −80° C.);
  Flash-freezing in liquid nitrogen;
  90% ethanol with subsequent silica-based desiccation;
  storage in commercially available solutions (e.g. formalternate, RNAlater, Allprotect Reagent);
  use of protein stabilisers (e.g. DNA binding proteins such as histones);
  preservation using an inert gas;
  a combination of the different preservation techniques mentioned above for extended storage times (e.g. at ambient temperature).

FIGS. 6A to 6E show an example of a write operation to write a new set of DNA molecules to a target site of the thermal control chip. More precisely, these figures show two separate write operations for writing sets of molecules to two different sites, first to site 2 and then to site 1 (where sites 1 and 2 could be any of the sites 54 of the thermal control chip 52).

Figure 6A:
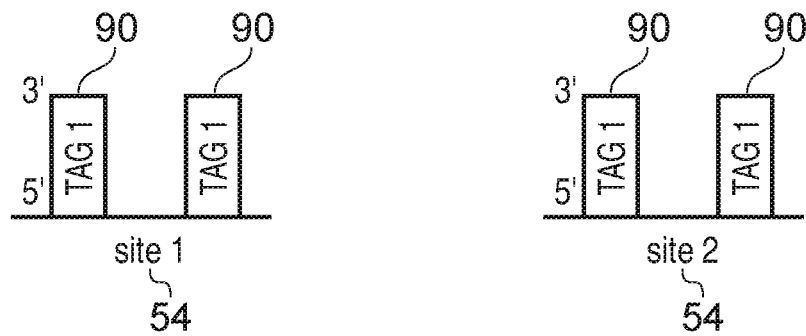

As shown in FIG. 6A, as an initial step the surface of each site 54 of the thermal control chip 52 is coated with a number of identical single-stranded tag fragments 90 corresponding to the complementary sequence of the address-independent first tag portion 62 of the bound strand 72 of each double-stranded DNA molecule which is to be stored at a given site. The tag fragments 90 are attached to the surface by the 5' end. The attachment of the tag fragments 90 to each site could be performed by covalent, ionic or dative surface attachment or by in-situ thermal synthesis of the tag fragments. The step of attaching the tag fragments 90 to each site could be done as a preliminary step when preparing the thermal control chip 52 for the very first write operation to be performed when there is no DNA yet stored on the thermal control chip 52.

Figure 6B:
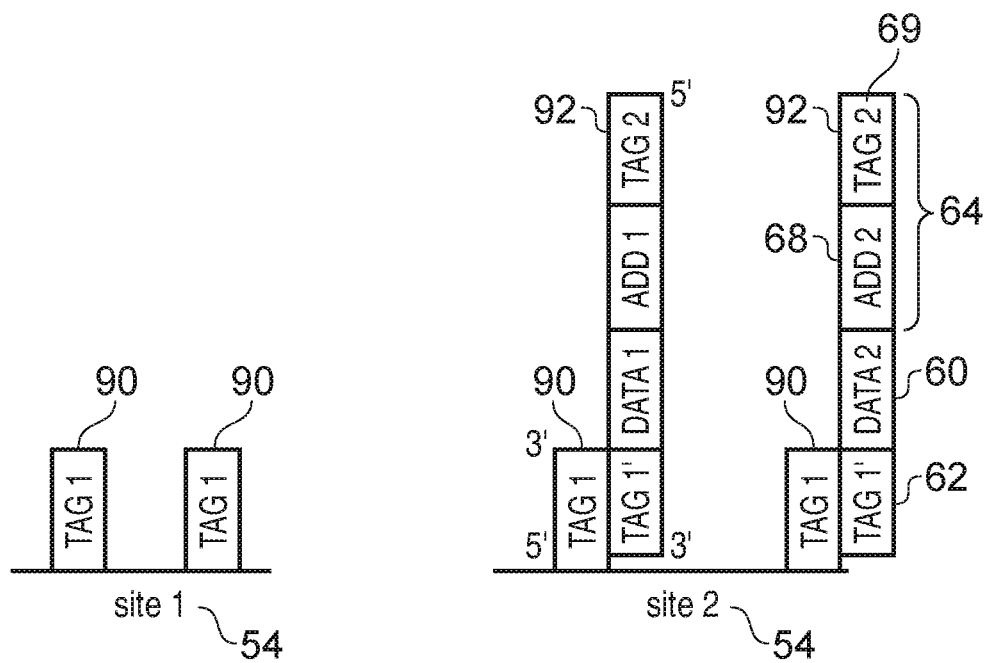

A write set of single-stranded DNA molecules 92 is prepared or obtained, with each single-stranded DNA molecule encoded with a sequence according to one of the desired double-stranded molecules 70 to be written to the target site. A first tag portion 62 (TAG 1') is provided at the 3' end of each single-stranded DNA molecule 92, with a sequence complementary to the tag fragments 90. A second tag portion 64 is provided at the 5' end of each of the single-stranded DNA molecules 92, where the second tag portion 64 includes an address-independent part (TAG 2) 69 closest to the 5' end, and an address-dependent part 68 immediately adjacent to the address-independent part 69. In the example of FIG. 6B, the target site is site 2. Each of the single-stranded molecules 92 of the write set are encoded with a data portion 60, first tag portion 62 and second tag portion 64 as shown in FIG. 5, with different address portions 68 included in the respective single-stranded molecules which have different data portions 60. The write set of DNA molecules 92 are flowed over the surface of the thermal control device 52 using the fluid flow path (e.g. a fluid flow cell) so that they are exposed to multiple sites of the thermal control device 52 (not only the target site). Meanwhile, temperatures at each site are controlled so that there is a greater probability of the write set of molecules 92 annealing to the tag fragments 90 at the target site compared to other sites. This is achieved by setting the temperature $T_2$ at the target site to a lower temperature than the melt temperature at which the tag fragments 90 are expected to separate from corresponding complementary sequences within the first tag portion 62, while other sites are set to a temperature $T_1$ which is greater than the melt temperature of the tag fragments 90.

Figure 6C:
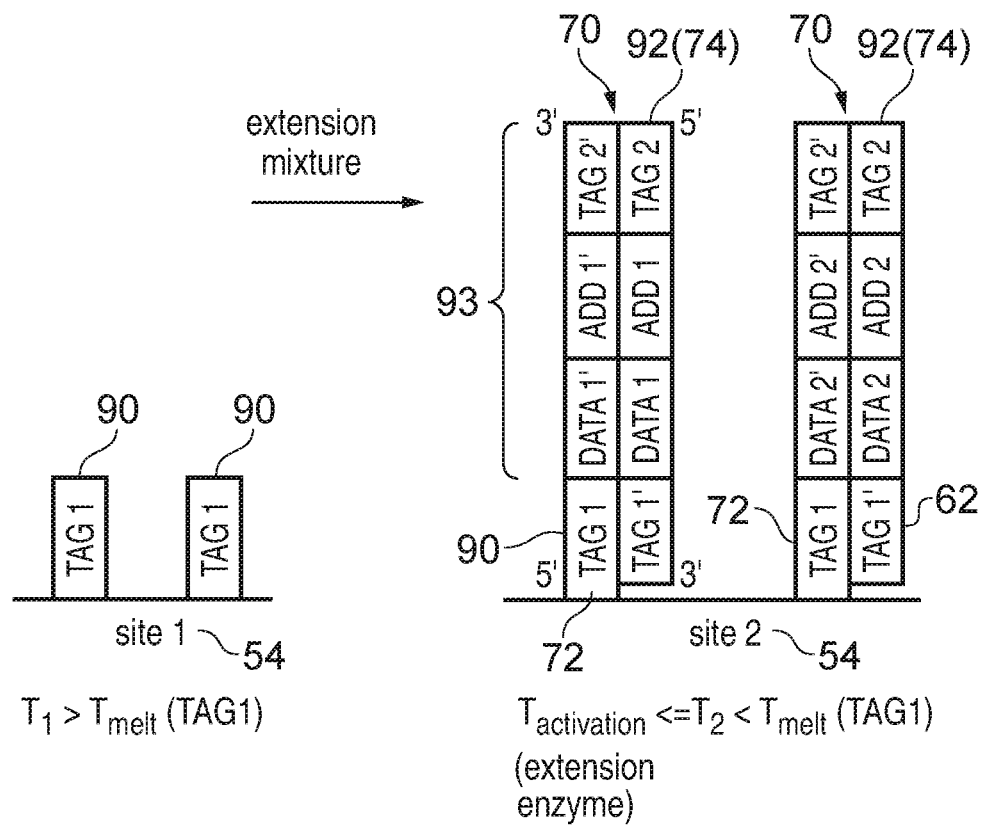

As shown in FIG. 6C, an extension mixture (e.g. comprising an extension enzyme such as polymerase and dNTPs) is introduced in the fluid flow path (and is exposed to multiple sites including the target site). The temperature $T_2$ at the target site is set to a temperature lower than the melt temperature of the TAG 1 portion 62 of the sequence but greater than or equal to an activation temperature for the extension mixture. Meanwhile the temperature $T_1$ at other sites is still set to a temperature higher than the melt temperature of the TAG 1 sequence. The extension enzyme extends the tag fragment 90 with bases 93 complementary to the remaining part of the single-stranded sequence 92 that is bound (hybridised) to the tag fragment 90, extending the tag fragment 90 in the 5' to 3' direction, so that the originally supplied write set of single-stranded molecules 92 become the loose strands 74 of each double-stranded DNA molecule 70 provided at the target site, and the extended sequences obtained by extending each tag fragment 90 become the bound strands 72.

Figure 6D:
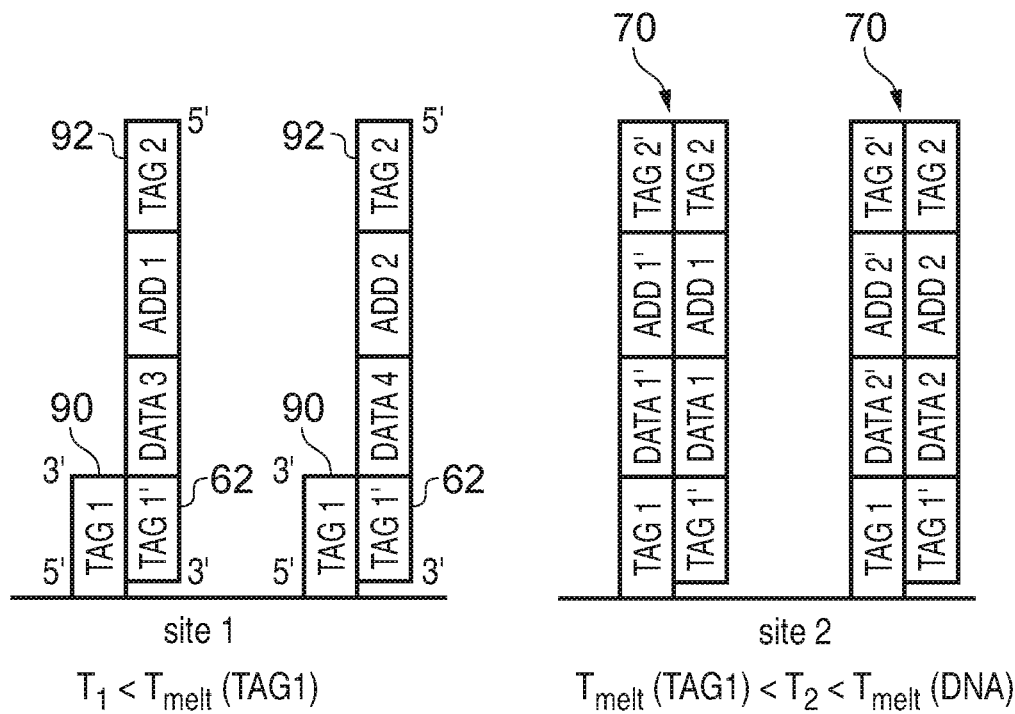

As shown in FIG. 6D having already written the set of double-stranded DNA molecules at site 2, a write operation can then be performed on site 1 without destroying the molecules already written to site 2, even though any supplied fluids are subjected to both the already written site 2 and the new target site 1. Again, a further set of single-stranded DNA molecules representing the encoded data is supplied within the fluid flow path so that it flows over the target site 1 and other sites, and again the temperature $T_1$ at the target site is set to lower than the expected melt temperature of the TAG 1 portion of the sequence while the temperature $T_2$ at any previously written sites is set to a temperature greater than the melt temperature of the TAG 1 sequence but less than the melt temperature of the overall DNA molecule 70. The temperature required to separate the longer DNA molecule 70 will be greater than the temperature required to separate DNA strands bonded only by the TAG 1 portion 90, 62, because the overall DNA molecule is bonded by complementarity between a greater number of bases. Hence, even though the temperature is raised higher than the melt temperature of the tags, the previously written DNA molecules 70 at site 2 do not dissociate.

Figure 6E:
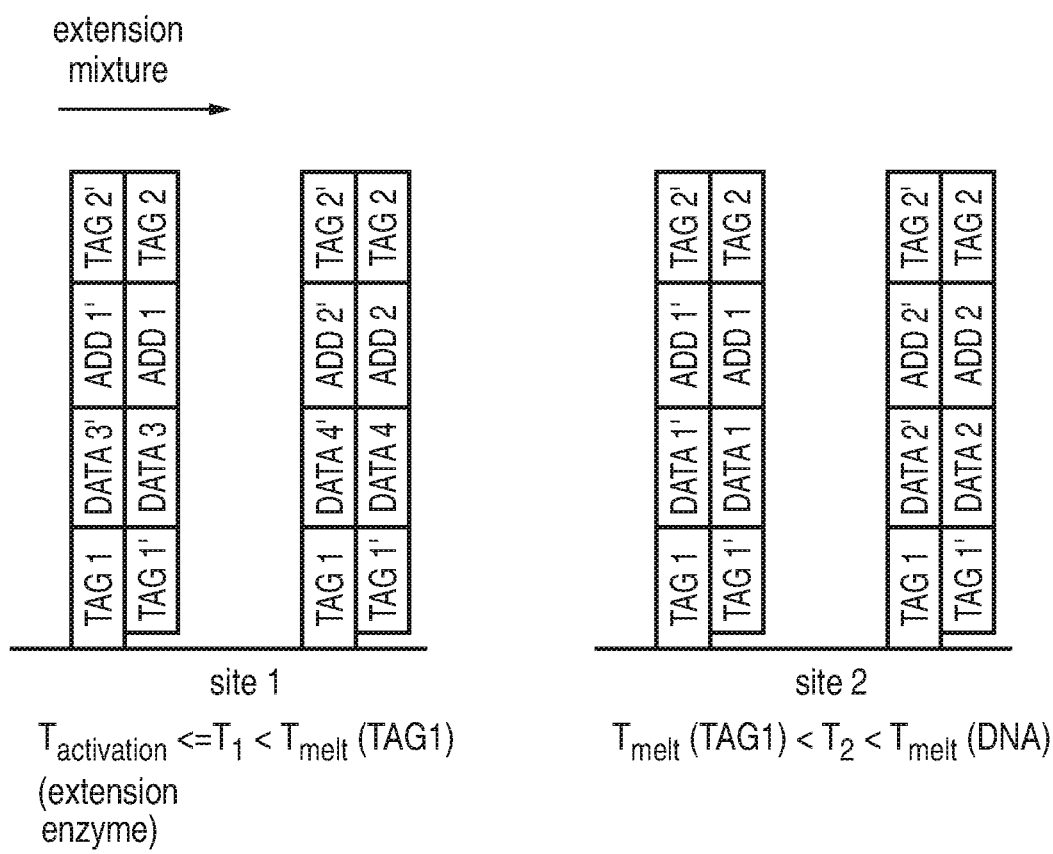

As shown in FIG. 6E the extension mixture can then be provided once more, again with the temperature $T_1$ at the target site being set greater than or equal to the activation temperature of the extension enzyme and lower than the melt temperature of the TAG 1 portion, while the temperature at previously written sites is set to greater than the melt temperature of the TAG 1 sequence and less than the melt temperature of the overall DNA.

In one example, in a write operation, the encoding and synthesis processes are completed for the largest data set that can be accommodated by a practical library of addressing primers. In addition to the error-correcting and addressing codes, each fragment has an identical sequence at end of the molecule, called the tag. Single-stranded DNA (oligonucleotides) are used instead of double-stranded molecules, which are combined into a single pool. The surface of the thermal control chip is coated with identical single-stranded DNA fragments, either by chemical attachment or in-situ thermal synthesis. These fragments are complementary to the tags at the end of the information-containing molecules. The information-containing molecules are introduced to the flow cell, with all but a single site held at a temperature higher than the annealing temperature of the tag. The information-containing molecules will anneal at the cold site, where the tags will keep them in place, but not at the hotter sites. This process is repeated for each of the sites with new information-containing molecules, therefore storing multiples of the largest practical data set.

FIG. 7 is a flow diagram showing a method of performing the write operation. At step 100 tag fragments 90 of single-stranded nucleic acid are provided bound to a surface of the target site 54 (tag fragments are also provided at other sites). The tag fragments are encoded with a sequence corresponding to the tag portion 62 of the bound strand 72 of each double-stranded molecule 70 to be written.

At step 102 the site temperatures are controlled by the temperature control circuitry 56 under control by the control computer 58, to provide a greater probability of a write set of molecules 92 annealing to the tag fragments 90 at the target site compared to other sites. In particular, the target site is set to a lower temperature than other sites. More particularly, the target site is set to a lower temperature than the melt temperature of a sequence corresponding to the tag fragments 90, while other sites are set to a higher temperature than the melt temperature of the TAG 1 sequence.

At step 104 the write set of single-stranded nucleic acid molecules is supplied by flowing fluid across the thermal control device. The fluid is exposed to multiple sites, not just the target site. Each single-stranded nucleic acid molecule is encoded with a data portion and an address portion (and also possibly an error correcting portion) and has a first tag portion which includes a sequence which is complementary to the tag fragments 90 provided at step 100 (also a second tag portion is included at the end of the molecule). The write set of single-stranded nucleic acid molecules may have been synthesised off-chip by any known DNA synthesis technique, or obtained from a commercial provider of encoded DNA sequences, with the encoding chosen according to particular data to be written. The lower temperature at the target site than the other site means that the write set of molecules are more likely to anneal to the tag fragments at the target site than at other sites.

At step 106 an extension mixture is applied, e.g. by flowing fluid containing the extension substance through the fluid flow cell across each site. The extension mixture, e.g. including an enzyme such as polymerase, acts to extend the tag fragment 90 with bases complementary to a remaining portion of the single-stranded nucleic acid molecule that is bound to the tag fragment 90. The result is a double-stranded DNA molecule 70 attached to the target site by the bound strand 72 which is encoded according to the desired data.

The method may cycle through steps 102 to 106 a number of times.

FIGS. 8A to 8D show an example of a read operation to read data encoded in the double-stranded DNA molecules 70 at a particular target site which match a target address portion, and a restore operation to restore double-stranded DNA molecules 70 which separate during the read operation. The target site is for sake of example considered to be site 2 and the target address portion to be read is ADD 1. Note that site 1 in the example of FIG. 8A also includes a molecule with the same address portion ADD 1, but this molecule has different data, DATA 3, compared to the data (DATA 1) in the actual molecules to be read.

Figure 8A:
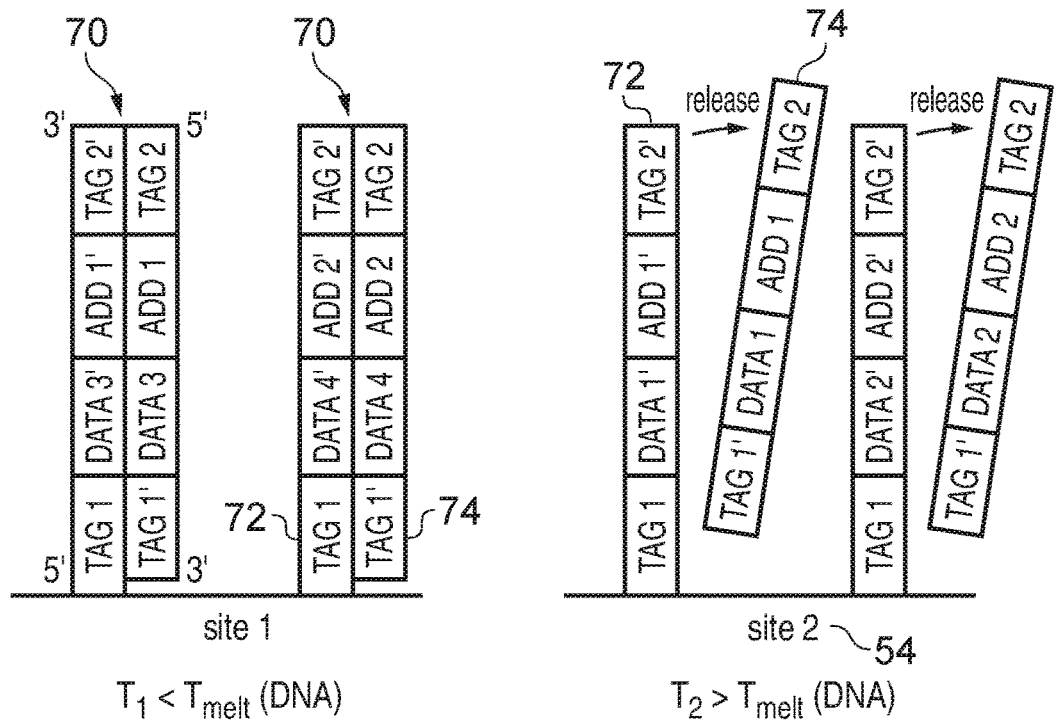

As shown in FIG. 8A, the target site $T_2$ is set to a temperature higher than the expected melt temperature of the double-stranded DNA molecules 70. Meanwhile, other sites which are not intended to be read, such as site 1 in this example, are set to a temperature less than the expected melt temperature of the DNA molecules. This means that the DNA molecules 70 at the target site (site 2) are more likely to separate into their bound 72 and loose strands 74 than at other sites. The bound strand 72 of each separated double-stranded molecule remains bound to a surface at the target site 54 while the loose strand 74 is free to flow away in the fluid, or can be corralled (e.g. using magnetic or electrostatic fields) to keep the loose strand local to the corresponding site.

Figure 8B:
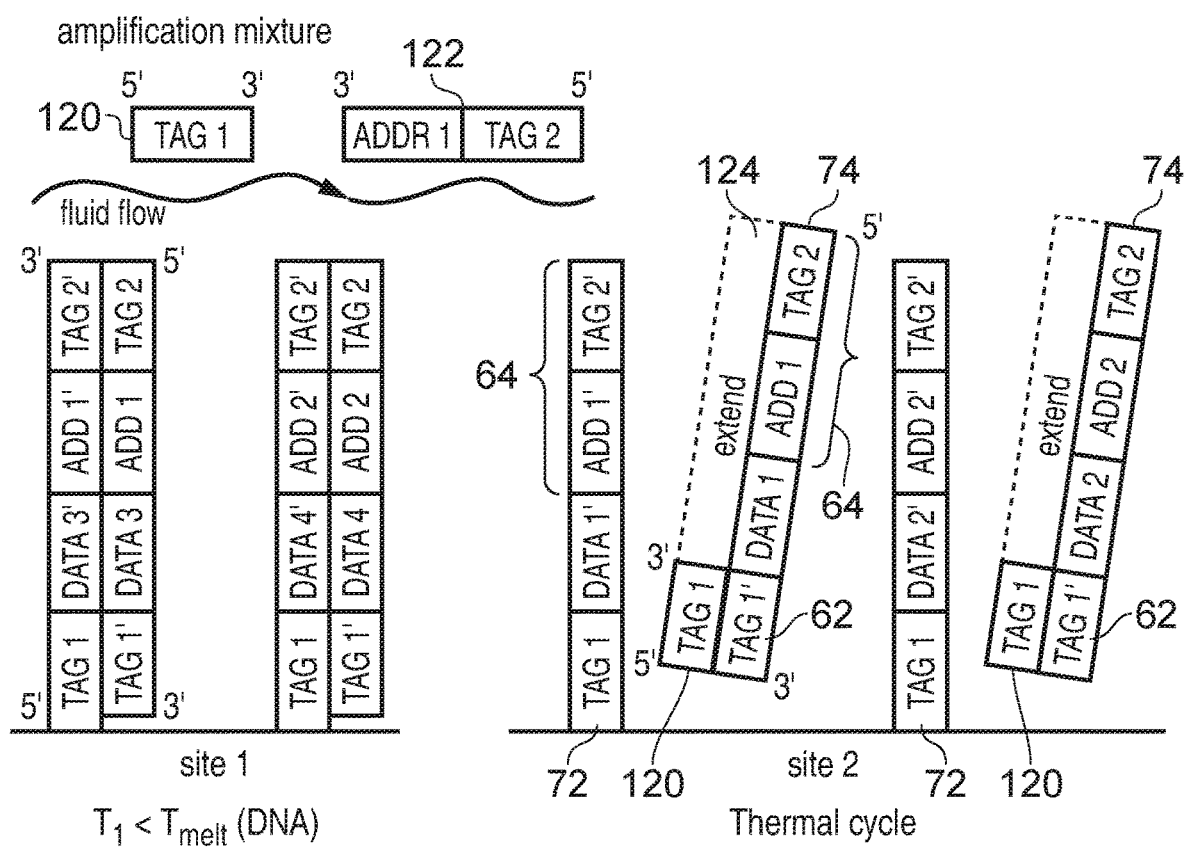

As shown at FIG. 8B, an amplification mixture (e.g. a PCR mixture) is exposed to multiple sites including the target site, by flowing the amplification mixture within a fluid flowing across the thermal control device. The amplification mixture includes a first primer 120 and a second primer 122. The first primer 120 is complementary to the sequence of bases in the first tag portion 62 of the loose strand 74 of the separated DNA molecules. The second primer is complementary to the second tag portion 64 within the bound strand 72. The amplification mixture may also include extension enzymes and other substances for activation of the enzymes. As shown in FIG. 8B, the first primer 120 binds to the first tag portion 62 at the 3' end of the loose strands 74 of single-stranded DNA which were separated in FIG. 8A. The temperature at the target site is thermally cycled to alternate between higher and lower temperatures, where the highest temperature of the cycle is higher than the melt temperature of DNA sequences having the length corresponding to the overall DNA molecules and the minimum temperature of the cycle is lower than the melt temperature of sequences corresponding to the first tag portion 62 and second tag portion 64. Meanwhile the temperature at sites other than the target site is set to a temperature lower than the melt temperature of DNA molecules having a sequence length corresponding to the length of the overall double-stranded molecule 70. As shown in FIG. 8B, when the first primer 120 bonds to the first tag portion 62 of the loose strand 74 of each separated DNA molecule, then the extension enzyme extends the primer with bases 124 complementary to the remaining portion of the loose strand, extending the sequence in the 5' to 3' direction, to produce a strand with the same sequence as in the bound strands 72 which are still attached to the surface of the target site. Meanwhile the DNA molecules at other sites have not separated and so are unaffected by the primers.

Figure 8C:
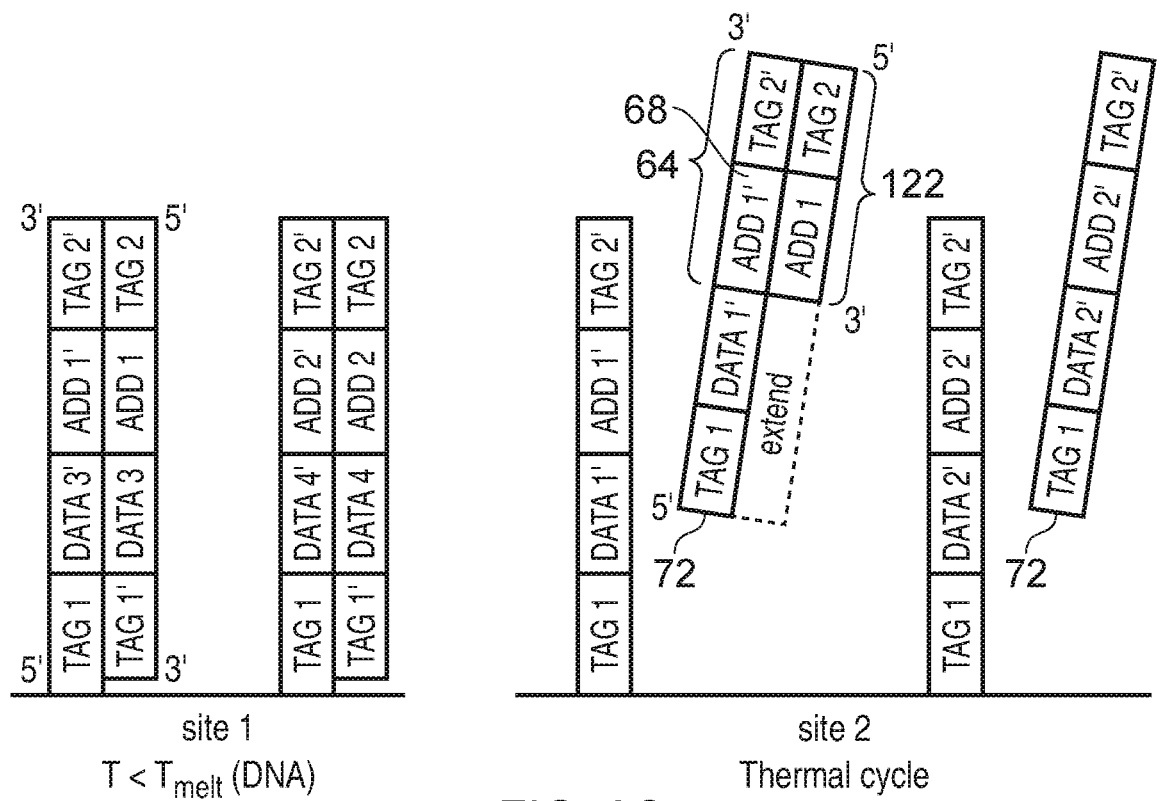

The thermal cycling means that the newly created sequence of bases extended from the primer then separates from the loose strand 74 so that effectively the bound strand 72 has been replicated as another single-stranded DNA molecule which is free from the surface of the target site. As shown in FIG. 8C, when the temperature is then reduced once more in the thermal cycle then the 3' end of the previously replicated bound strand 72 bonds to the second primer 122 of the amplification mixture in the molecules which have the address portion 68 matching the target address portion. Hence in the example of FIG. 8C the primer bonds to a strand of DNA having a first address portion ADD 1 matching the corresponding target address portion in the primer, but does not bind to another strand 72 which has a different address portion ADD 2. Again, the sequence of the second primer 122 is extended in the 5' to 3' direction with bases complementary to the remaining part of the replicated bound strand 72. Although not shown in FIG. 8C, primer 122 can also hybridise with the bound strand 72 which remains bound to the surface, and extend in the 5' to 3' direction, providing more amplification at the surface.

The steps shown in FIGS. 8A, 8B and 8C may in practice be performed simultaneously and the process may cycle through a number of repetitions of each of these steps, alternating between a higher temperature of the thermal cycle when previously bound double-stranded molecules are separated into single strands, and a lower temperature of the thermal cycle when the primers bound to the relevant tag portion of separated strands of single-stranded DNA and the primers are extended with bases complementary to the remaining sequence so as to replicate a strand of DNA. By repeating this a number of times, the use of an address-specific primer 122 means that the strands corresponding to a molecule having the target address portion ADD 1 are more likely to be amplified than the strands having a different address portion, so that a large number of copies of the molecules having the target address sequence ADD 1 are provided, which can then be supplied to a sequencer for sequencing and decoding.

In the examples shown above, the address-specific primer 122 fully matches the second tag portion 64 including both the address-independent part labelled TAG 2 and the address-dependent part with an address portion varying from molecule to molecule at the target site. However, it is not essential to have the primer 122 fully matching the address portion, and in some cases a partial match against the address portion in molecules at the target site can be enough to enable at least some of the molecules having the wrong address portion to be discarded in the amplification process, with the remaining molecules which do share the partial matching against the address portion in the address-specific primer 122 being distinguished by identifying the full address portion during the sequencing step.

In the example of FIGS. 8B and 8C, primer 120 is an address-independent primer, so there will be copying of strands with the "wrong" address portion, but only in one direction, since the other primer 122 is an address-dependent primer. Hence, although there is some copying of strands with the "wrong" address, the "correct" strands with the target address will come to dominate because they are copied in both directions. As discussed below with respect to FIG. 12, if both primers 120, 122 are address-dependent then the "wrong" strands would not be copied at all.

Also, FIGS. 8B and 8C show an example in which an address-specific primer 122 is supplied in the amplification mixture, to selectively amplify the DNA molecules which have an address portion at least partially matching the target address portion. However, another option for a read operation is to supply an amplification mixture comprising two address-independent primers, where the first primer 120 is the same as in FIGS. 8B and 8C but the second primer is complementary to the address-independent part (TAG 2) of the second tag portion 64 of the bound strand 72 of each molecule (i.e. the second primer may be the same as the restoration primer 130 discussed below). With such an address-independent amplification mixture, all the data (i.e. the whole address range) encoded in the double-stranded DNA molecules at a single site could be extracted from the site for supply to a sequencer. The sequencer can read the data and address portions of each molecule and reassemble the binary data set represented by the double-stranded DNA molecules.

The examples of FIG. 8A to 8C show performing the amplification locally on the chip, but it is also possible following the release of the loose strand 74 of DNA as shown in FIG. 8A to flow the loose strands off-chip in the fluid flow channel and then to perform the thermal cycling and amplification off-chip ready for sequencing.

FIGS. 8B and 8C show an example of using PCR to perform the amplification, but other methods can also be used to amplify selectively the DNA sequences to have an address portion at least partially matching a target address portion. For example, isothermal enzyme-based amplification methods can be used as discussed in the paper by Fakruddin et al. cited above.

Figure 8D:
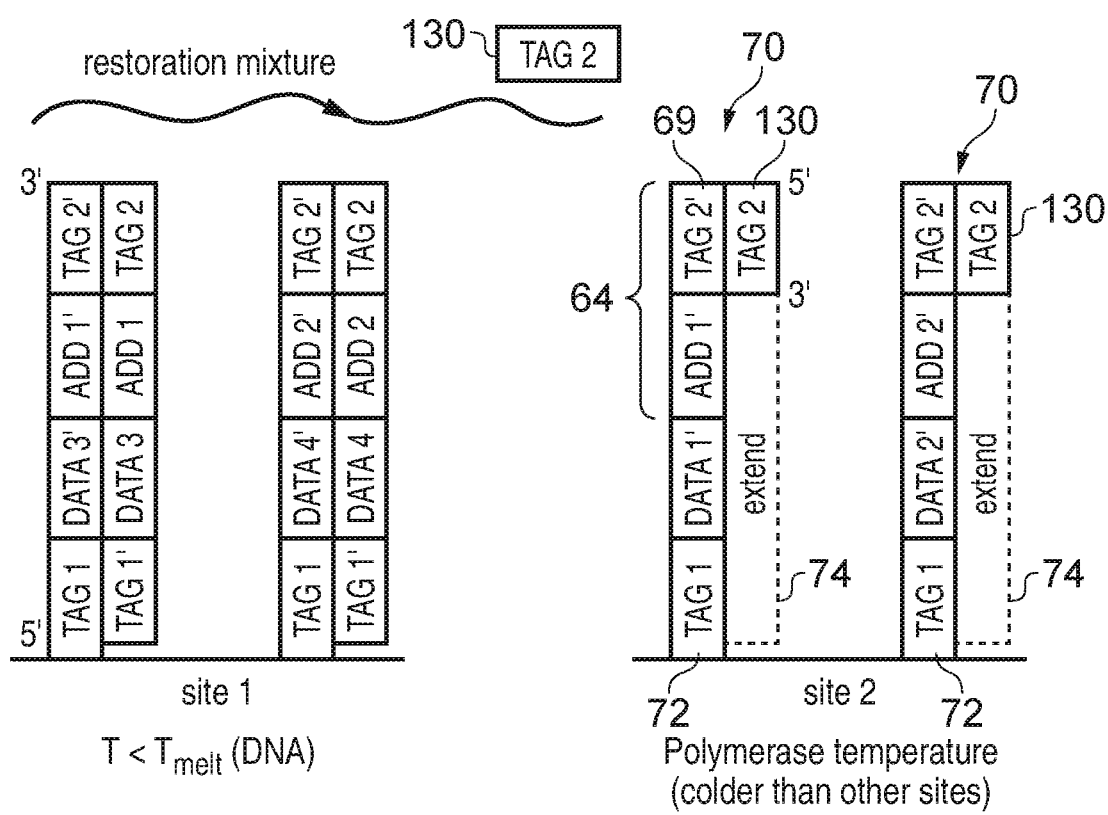

As shown in FIG. 8D, after separating the double-stranded molecules at the target site ready for any amplification and sequencing, and removing any copied strands from the flow cell, the original double-stranded molecules 70 can later be restored by supplying a restoration primer 130 (TAG 2) which is complementary to the address-independent part 69 of the bound strand 72 of each double-stranded DNA molecule 70 at the target site.

During the restoration operation, the sites other than the target site are set to a temperature lower than the expected melt temperature of the DNA sequence as a whole, but above the melting temperature of TAG2, while the target site is set to a colder temperature than other sites, to a temperature equal to or higher than an activation temperature required for activation of a polymerase enzyme or other extension enzyme for extending sequences of DNA. Because the target site is at a lower temperature than other sites, the restoration primer 130 is more likely to anneal to the address-independent part 69 of the second tag portion 64 of the bound strand 72 remaining at the target site (the primer 130 attaches to the 5' end of the bound strand 72). By providing an address-independent primer as the restoration primer 130, this enables restoration of all of the double-stranded molecules which separated during the read process, not just the molecules which have the address-portion matching the target address portion to be read. The primer 130 bonds to the address-independent part of the bound strands 72, and then the extension enzyme extends the restoration primer 130 with bases complementary to the remaining part of the bound strand 72 so as to recreate the loose strand 74 which previously separated from the bound strand 72 during the read process. Hence the target site is restored to the state it was in before the read operation was performed, so that the data can be read again at a later time without needing to supply a new write set of encoded single-stranded DNA.

In some examples the restoration step of FIG. 8D could be performed at the same time as earlier steps in FIGS. 8A-8C, e.g. by supplying the restoration mixture at the same time as the amplification mixture and using the cooler part of the thermal cycle to cause the restoration to be performed.

Hence, in one example in the read operation an amplification mixture (e.g. PCR mixture) is introduced into the flow cell. A single target site is thermally cycled, above the DNA melt temperature and below the primer/tag annealing temperature. When the site is hot the tags will melt, and the molecules will be released into solution, where the thermal cycling will cause amplification. When the site is cold, amplified molecules will re-anneal with the tags, ensuring that the data is preserved on the site. The excess amplified molecules can be removed from the flow cell. Individual molecules can be addressed by using primers that are complementary to the desired address, either during the on-chip amplification or in a second-stage off-chip process. The decoding process proceeds as before, except that the sequence of tags is discarded.

FIG. 9 is a flow diagram showing a method of performing a read operation to DNA based data storage or storage using other nucleic acids. At step 150 a target site 54 of the thermal control chip is set to a higher temperature than other sites to provide a greater probability that double-stranded nucleic acid molecules 70 at the target site will separate into single strands compared to other sites of the thermal control device 52.

At step 152, either on-chip or off-chip, the separated single-stranded nucleic acid molecules are exposed to an amplification mixture which includes at least one primer for selectively amplifying single-stranded nucleic acid molecules which were separated from double-stranded nucleic acid molecules having an address portion at least partially matching a target address portion. If the amplification is performed on-chip then the temperature at the target site may be set differently to other sites, by controlling the temperatures according to a thermal cycle if amplification is being performed by PCR. If isothermal enzyme-based methods are being used then, once the double-stranded nucleic acid molecules have separated at the target site, it is not essential to continue to provide different temperatures at the target site compared to the other sites, as the enzyme-based method may act on separated single-stranded nucleic acid molecules at the target site but not on the still intact double-stranded nucleic acid molecules at other sites (hence during the amplification the target site, and optionally other sites, may be set to a temperature greater than or equal to an activation temperature of the amplification enzyme, but lower than the melting temperature of the whole DNA molecule). If the amplification is performed off-chip then instead the temperature control may be applied to a vessel into which the separated molecules are provided after being removed from the thermal control chip 52.

Having amplified the separated single-strands using the amplification mixture, which due to the presence of at least one address-specific primer is more likely to amplify the molecules having the target address portion than the molecules having other address portions, and which due to the temperature control is more likely to amplify molecules at the target site than at other sites even if there are molecules having the same address portion as the target address portion at other sites, this means that the amplified molecules are a pool of molecules which are expected with a reasonable probability to largely contain amplified molecules having the matching address portion. At step 154 the amplified molecules are sequenced to identify at least the data portion 60 of those molecules (and possibly also an error correction portion and optionally also an address portion if the primer using the amplification mixture was not fully matching against the address portion of the amplified molecules). Based on the sequencing, the sequence of bases can be identified and hence the data that was encoded in that sequence can be decoded to reconstruct the original data which was written to the thermal control device.

At step 156 the double-stranded nucleic acid molecules which separated at step 150 are restored by setting the target sites to a lower temperature than other sites and applying a restoration mixture which comprises a restoration primer for annealing with at least part of a tag portion at one end of a bound strand 72 of each separated double-stranded nucleic acid molecules 70. The restoration mixture also includes an extension substance for extending the sequence of bases of the restoration primer once bound to the bound strands 72 with bases complementary to the remaining portions of the bound strands, so as to reconstruct the double-stranded nucleic acid molecules.

If it is desired to erase the data in the DNA based storage then the information containing fragments of DNA 70 can be removed from a site by increasing the temperature of the site to above the melt temperature of the double-stranded DNA. The strands will melt and the waste fragments can be removed from the flow cell. The bound single-stranded DNA can then be degraded using an exonuclease or other method, and initial tags can be re-introduced to prepare for the next write cycle.

It can be useful to provide a relatively high surface area at each site for attachment of single or double-stranded DNA molecules. By providing attachment surfaces which have a greater total surface area compared to a projection of the target site onto the substrate of the thermal control device, this can provide more space for attaching DNA molecules and hence improved DNA storage density. FIGS. 10 and 11 show two examples for increasing the effective surface area of a site. As shown in FIG. 10, a number of beads 200 can be immobilised above a given site 54 of the thermal control device, e.g. by physically attaching the beads to the site or by immobilising the beads above the site by using an electrostatic or magnetic field for example. Alternatively as shown in FIG. 11 the surface of a given site can be patterned in a three-dimensional structure e.g. using ridges and valleys, to increase the effective surface area.

In the examples shown above, the first tag 62 is an address-independent tag and the second tag is an address-dependent tag 64. However, as shown in FIG. 12 it is also possible to encode the DNA sequences so that the tags at both ends of the DNA module are address-specific tags which include a portion of the address portion of the molecule. Hence, both the first and second tag 62, 64 may include part of the address portion and the overall address of the DNA molecule may be formed by the combination of the address portions (ADD1a, ADD1b) at either end of the molecule. This approach can help to improve the selectivity of read access. When the DNA is encoded in this manner then both the first and second primers 120, 122 used in the read amplification mixture may be address-specific primers which include a part which matches against the corresponding portion of the address portion in the molecules to be read. The restoration mixture may still include an address-independent primer which matches against an address independent part of the second tag 64 in all molecules at a given site. By using address-specific tags at both ends, this means that the total number of primers which need to be maintained for reading a given set of addresses can be reduced, since the address selection is based on a combination of a specifically selected first primer matching a target address portion and a specifically selected second primer 122 matching the target address portion. E.g. a combination of ten different first primers and ten different second primers can provide a hundred different possible combinations to match against a hundred different address patterns using only 20 primers. In this case, the DNA storage access circuitry may include elements to store the different libraries of primers available for selection as the first primer 120 and the second primer 122, and for combining these according to the particular address to be read before providing the amplification mixture to the chip.

Although illustrative embodiments of the invention have been described in detail herein with reference to the accompanying drawings, it is to be understood that the invention is not limited to those precise embodiments, and that various changes and modifications can be effected therein by one skilled in the art without departing from the scope and spirit of the invention as defined by the appended claims.

The invention claimed is:

1. A method for accessing data storage provided using double-stranded nucleic acid molecules provided on a thermal control device comprising a plurality of sites and temperature control circuitry to independently control a temperature of each of the plurality of sites;
the method comprising:
controlling temperatures of the plurality of sites using the temperature control circuitry, to provide a different temperature at a target site compared to other sites of the plurality of sites; and
performing a read operation to read data from one or more selected double-stranded nucleic acid molecules at the target site or a write operation to form one or more new double-stranded nucleic acid molecules encoded with data at the target site, where the different temperatures at the target site and the other sites provide a greater probability of the read or write operation acting on the target site compared to the other sites.

2. The method of claim 1, in which the plurality of sites are at respective portions of a shared fluid well, without a physical barrier blocking fluid from passing between adjacent sites.

3. The method of any of claim 1, in which the read operation or the write operation comprises flowing fluid across at least two of the plurality of sites including the target site.

4. The method of claim 1, in which:
each double-stranded nucleic acid molecule includes at least a data portion and an address portion;
double-stranded nucleic acid molecules with different data portions but the same address portion are provided at different sites of the thermal control device; and
at a given site of the thermal control device the double-stranded nucleic acid molecules located at the given site which have different data portions also have different address portions.

5. The method of claim 1, in which when a read operation is performed, said controlling temperatures comprises setting the target site to a higher temperature than the other sites during at least part of the read operation, to provide a greater probability of the double-stranded nucleic acid molecules separating into single-stranded nucleic acid molecules at the target site than at the other sites.

6. The method of claim 5, in which the read operation comprises restoring the double-stranded nucleic acid molecules which were separated into single-stranded nucleic acid molecules.

7. The method of claim 6, in which each double-stranded nucleic acid molecule comprises a bound strand which is bound to a surface at one of the plurality of sites, and a further strand which is bound to the bound strand; and
the restoring comprises applying a restoration mixture comprising a restoration primer for annealing with at least part of a tag portion at one end of the bound strand of each separated double-stranded nucleic acid molecule.

8. The method of claim 7, in which the tag portion includes an address-independent part which is the same for double-stranded nucleic acid molecules having different address portions at a given site, and the restoration primer is complementary to the address-independent part.

9. The method of claim 6, in which during the restoring, the target site is maintained at a lower temperature than other sites.

10. The method of claim 1, in which each double-stranded nucleic acid molecule includes at least a data portion and an address portion, and the read operation comprises:
exposing separated single-stranded nucleic acid molecules to an amplification mixture comprising at least one primer for selectively amplifying a single-stranded nucleic acid molecule separated from a double-stranded nucleic acid molecule having an address portion at least partially matching a target address portion; and
sequencing amplified nucleic acid molecules amplified by the amplification mixture to identify at least the data portion of the amplified nucleic acid molecules.

11. The method of claim 6, in which each double-stranded nucleic acid molecule comprises first and second tag portions at opposite ends of the double-stranded nucleic acid molecule; and
at least one of the first and second tag portions is an address-specific tag portion which includes at least part of the address portion of the double-stranded nucleic acid molecule.

12. The method of claim 7, in which the amplification mixture comprises:
a first primer complementary to the first tag portion of a first strand of a double-stranded nucleic acid molecule having a target address portion; and
a second primer complementary to the second tag portion of a second strand of the double-stranded nucleic acid molecule having the target address portion.

13. The method of claim 11, in which one of the first and second tag portions is an address-independent tag portion which is the same for double-stranded nucleic acid molecules having different address portions at the same site.

14. The method of claim 11, in which both the first tag portion and the second tag portion are address-specific tag portions.

15. The method of claim 11, in which at least one of the first tag portion and the second tag portion is an address-specific tag portion comprising:
- an address-dependent part comprising at least part of said address portion; and
- an address-independent part which is the same for double-stranded nucleic acid molecules having different address portions at the same site.

16. The method of claim 10, in which the amplification mixture is applied to the plurality of sites to amplify the released single-stranded nucleic acid molecules locally on the thermal control device.

17. The method of claim 16, in which the amplification is performed by one of:
- PCR, where said controlling temperatures comprises thermal cycling of the target site through repeated cycles of heating and cooling, while maintaining other sites at a temperature lower than a maximum temperature used in said thermal cycling; and
- an isothermal enzyme-based amplification method, where said controlling temperatures comprises setting the temperature of the target site to a temperature greater than or equal to an activation temperature of at least one amplification-dependent enzyme.

18. The method of claim 10, in which the amplification mixture is applied to the separated single-stranded nucleic acid molecules after removal of the separated single-stranded nucleic acid molecules from the thermal control device.

19. The method of claim 1, in which when a write operation is performed, the target site is maintained at a lower temperature than other sites, to provide a greater probability of the new double-stranded nucleic acid molecules forming at the target site compared to other sites.

20. The method of claim 1, in which the write operation comprises:
- providing tag fragments of single-stranded nucleic acid bound to a surface at the target site; and
- supplying a write set of single-stranded nucleic acid molecules corresponding to the new double-stranded nucleic acid molecules, each of the write set of single-stranded nucleic acid molecules including a tag portion complementary to the tag fragments, said different temperature at the target site providing a greater probability of the write set of single-stranded nucleic acid molecules annealing to the tag fragments at the target site compared to other sites.

21. The method of claim 20, in which the write operation also comprises applying an extension mixture to extend each tag fragment with bases complementary to a remaining portion of the single-stranded nucleic acid molecule that annealed to that tag fragment, to form a corresponding double-stranded nucleic acid molecule.

22. The method of claim 20, in which the write set of single-stranded nucleic acid molecules is exposed to at least two sites of the thermal control device including the target site.

23. The method of claim 1, in which the thermal control device comprises a substrate, and the plurality of sites are disposed at respective locations on the substrate;
- each site comprises at least one attachment surface for attaching single or double-stranded nucleic acid molecules; and
- a total surface area of said at least one attachment surface at a given site is greater than an area of a projection of the given site onto the plane of the substrate.

24. The method of claim 1, in which the thermal control device comprises:
- a plurality of active thermal regions disposed at respective locations on a substrate, each active thermal region comprising a heating element configured to apply a variable amount of heat to a corresponding one of the plurality of sites, and a thermal insulation layer disposed between the heating element and the substrate; and
- one or more passive thermal regions disposed between the plurality of active thermal regions on the substrate, each passive thermal region comprising a thermal conduction layer configured to conduct heat to the substrate;
- in which the thermal conduction layer of said one or more passive thermal regions has a lower thermal resistance in a direction perpendicular to a plane of the substrate than the thermal insulation layer of said plurality of active thermal regions.

25. A non-transitory computer-readable program or data structure comprising instructions or control data for controlling an apparatus to perform the method of claim 1.

* * * * *